(12) United States Patent
Goldstein et al.

(10) Patent No.: US 6,207,403 B1
(45) Date of Patent: Mar. 27, 2001

(54) KINESIN MOTOR MODULATORS DERIVED FROM THE MARINE SPONGE ADOCIA

(75) Inventors: Lawrence S. B. Goldstein, San Diego; David John Faulkner, La Jolla; Roman Sakowicz, Foster City; Michael S. Berdelis, Downey; Christine L. Blackburn, San Diego, all of CA (US); Cordula Hopmann, Frankfurt am Main (DE)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/226,772

(22) Filed: Jan. 6, 1999

Related U.S. Application Data

(60) Provisional application No. 60/070,772, filed on Jan. 8, 1998.

(51) Int. Cl.[7] .............................. C12Q 1/42; C12Q 1/68; G01N 33/53

(52) U.S. Cl. ........................... 435/21; 435/7.1; 435/6; 514/172; 514/182; 514/518; 585/350

(58) Field of Search ................... 435/21, 7.1, 6; 514/172, 182, 518; 585/350

(56) References Cited

U.S. PATENT DOCUMENTS

| | | | |
|---|---|---|---|
| 4,729,996 | 3/1988 | Wright et al. | 514/215 |
| 4,808,590 | 2/1989 | Higa et al. | 514/272 |
| 4,866,084 | 9/1989 | Gunasekera et al. | 514/397 |
| 4,970,226 | 11/1990 | Sun et al. | 514/397 |
| 5,574,057 | 11/1996 | Ireland et al. | 514/390 |

FOREIGN PATENT DOCUMENTS

9934806 A1 * 7/1999 (WO) .

OTHER PUBLICATIONS

Blackburn et al, "Science", vol. 280 (5361), p 292–295, 1998.*

Blackburn et al, "J. Org. Chem.", vol. 64(15), p 5565–5570, 1999.*

Minale, L., et al., "Avarol, a Novel Sesquiterpenoid Hydroquinone with a Rearranged Drimane Skeleton from the Sponge Disidea Avara" *Tetrahedron Letters*, 38:3401–3404 (1974).

de Rosa, S., et al., "The Absolute Configuration of Avarol, a Rearranged Sesquiterpenoid Hydroquinone From a Marine Sponge" *Journal of the Chemical Society, Perkins Transactions I*, 13:1408–1414 (1976).

Djura, P., et al., "Some Metabolites of the Marine Sponges *Smenospongia aurea* and *Smenospongia (=Polyfibrospongia) Echina*" *J. of Org. Chem.*, 45(8):1435–1441 (1980).

Walker, R., et al., "Diterpenes From the Sponge *Dysidea Amblia*" *J. Org. Chem.*, 46(6):1098–1102 (1981).

Gonzalez, A., et al., "Diterpenoids of Mixed Biogenesis in Phaeophyta Biogenetic–Type Interconversions" *Tetrahedron*, 38(5):719–728 (1982).

Cimino, G., et al., "Disidein, A Pentacyclic Sesterterpene Condensed with an Hydroxyhydroquinone Moiety, From the Sponge *Disidea Pallescens*" *Tetrahedron*, 31:271–275 (1975).

Cimino, G., et al., "Absolute Stereochemistry of Disidein and Two New Related Halogenated Sesterterpenoids. Two–Dimensional NMR Studies and X–Ray Crystal Structure" *Tetrahedron*, 43(20):4777–4784 (1987).

(List continued on next page.)

*Primary Examiner*—Louise N. Leary
(74) *Attorney, Agent, or Firm*—Medlen & Carroll, LLP

(57) ABSTRACT

This invention provides novel compounds derived from a marine sponge, Adocia sp., that specifically modulat kinesin activity by targeting the kinesin motor domain and mimicking the activity a microtubule. The compounds act as potent anti-mitogens are useful in a wide variety of in vitro and in vivo applications.

17 Claims, 6 Drawing Sheets

OTHER PUBLICATIONS

De Pasquale, R., et al., "Pharmacological Studies on Terpenoids from Marine Sponges: Analgesic and Muscle Relaxant Effects" *Phytotherapy Research*, 5(2):49–53 (1991).

Sakowicz, R. et al., "A Marine Natural Product Inhibitor of Kinesin Motors" *Science*, 280:292–295 (1998).

Woehlke, Gunther, et al., "Microtuble Interaction Site of the Kinesin Motor," *Cell*, 90:2070–216 (Jul. 25, 1997).

Sosa, Hernando, et al., "A Model for the Microtuble–Ncd Motor Protein Complex Obtained by Cryo–Electron Microscopy and Image Analysis,"*Cell*, 90:217–224 (Jul. 25, 1997).

Yang, Joy T., et al., "A Three–Domain Structure of kinesin Heavy Chain Revealed by DNA Sequence and Microtuble Binding Analyses,"*Cell*, 56:879–889 (Mar. 10, 1989).

Tucker, Carla, et al., "Probing the Kinesin–Microtuble Interaction,"*J. of Biol. Chem.*, 272(14):9481–9488 (Apr. 4, 1997).

Shimizu, Takashi, et al., "Nucleotide Specificity of the Enzymatic and Motile Activities of Dynein, Kinesin, and Heavy Meromyosin,"*J. Cell Biol.*, 112(6):1189–197 (Mar. 19991).

* cited by examiner

KINESIN MOTOR MODULATORS DERIVED FROM THE MARINE SPONGE ADOCIA

CROSS-REFERENCE TO RELATED INVENTIONS

This is a continuation-in-part of U.S. Provisional application Ser. No. 60/070,772, filed on Jan. 8, 1998, which is herein incorporated by reference in its entirety for all purposes.

STATEMENT AS TO RIGHTS TO INVENTIONS MADE UNDER FEDERALLY SPONSORED RESEARCH AND DEVELOPMENT

This invention was made with Government support under Grant No. GM 35252, awarded by the National Institutes of Health. The Government of the United States of America may have certain rights in this invention.

BACKGROUND OF THE INVENTION

Plants and animals have yielded a number of chemical molecules having useful biological activity (e.g., anti-tumor activity). Particularly rich sources of biologically active chemicals are marine organisms, which comprise over half a million species. Marine organisms have been found to produce a variety of metabolic often having unprecedented chemical structures.

In recent years, an increasing number of natural products extracted from marine organisms have been reported to exhibit a variety of biological activities such as antimicrobial, antiviral, antifungal and anticancer activities. These include peptides, polyethers, alkaloids, prostanoids, and the like. Such compounds have been obtained from sponges, octocorals, algae, tunicates, nuclibranches, bryozoans and marine bacteria.

In particular, a number of anti-tumor and anti-fungal compounds have been extracted from marine life. For example, U.S. Pat. No. 4,729,996 discloses anti-tumor imidazole ring compounds isolated from the marine sponges *Teichaxinella morchella* and *Ptioocaulis walpersi*. U.S. Pat. No. 4,808,590 discloses nitrogen containing cyclic compounds isolated having antiviral, anti-tumor, and antifungal properties, isolated from the marine sponge Theoneloa sp. Similarly, U.S. Pat. No. 4,866,084 discloses bisindole alkaloids extracted from the marine sponge *Spongosorites ruetzleri* useful in treating certain classes of tumors, while U.S. Pat. No. 4,970,226 discloses bis-indole imidazole alkaloids and derivatives isolated from the marine sponge Spongosorites sp. which exhibit useful anti-tumor and antimicrobial properties.

Marine sponges, in particular, have proven to be a rich resource for biologically active compounds (see, e.g., Scheuer, P. J. (ed.) (1978–1983) *Marine Natural Products, Chemical and Biological Perspectives Vol. I–V*, Academic Press, New York; Faulkner (1977) *Tetrahedron*, 33: 1421; Faulkner (1984) *Nat, Prod. Rep.* 1: 551; Faulkner (1986) *Nat, Prod. Rep.* 3: 1; Faulkner (1987) *Nat, Prod. Rep.* 4: 539; Faulkner (1988) *Nat, Prod. Rep.* 5: 613; Faulkner (1990) *Nat, Prod. Rep.* 7: 269; Faulkner (1991) *Nat, Prod. Rep.* 7: 269; Faulkner (1992) *Nat, Prod. Rep.* 9: 323; Faulkner (1993) *Nat, Prod. Rep.* 10: 497; Faulkner (1994) *Nat, Prod. Rep.* 1 1: 355; Faulkner (1954) *Nat, Prod. Rep.* 12: 223; Faulkner (1996) *Nat, Prod. Rep.* 13: 75; Faulkner (1997) *Nat, Prod. Rep.* 14: 256; and Faulkner (1985) *J. Am. Chem. Soc.* 107: 4796–4798). However there exist literally thousands of species of marine sponges and these organisms are only beginning to be explored.

SUMMARY OF THE INVENTION

This invention provides novel compounds derived from a marine sponge, Haliclona (aka Adocia) sp., that specifically modulate (e.g., inhibit) kinesin activity by targeting the kinesin motor domain and mimicking the activity a microtubule. It is believed this mode of kinesin motor modulation is previously unknown. Thus, it was also a discovery of this invention that the kinesin-microtubule interaction site is a useful target for small molecule modulators of kinesin motor activity.

Because the compounds were initially derived from the marine sponge Haliclona (Adocia) sp. they are referred to herein as Adocia compounds or Adocia-derived compounds. Particularly preferred Adocia-derived compounds are adociasulfates. Thus, in one embodiment, this invention provides for the Adocia-derived compounds having the formulas shown herein, more preferably for the adociasulfate compounds having the formulas shown herein.

The Adocia-derived compounds are potent kinesin motor modulators that appear to block kinesin binding of microtubules. The compounds are potent anti-mitotic agents that are highly effective in vitro and in vivo. Thus, in another embodiment, this invention provides composition for the in vivo modulation (e.g., inhibition) of kinesin motor activity (e.g., in a cell). The compositions typically comprise any of the Adocia-derived kinesin motor inhibitors described herein in combination with a pharmacologically acceptable excipient.

In another embodiment, this invention provides methods of modulating (e.g., inhibiting) kinesin motor activity in a cell. The methods involve contacting the cell with one or more of the Adocia-derived kinesin modulators described herein. The cell, although preferably a mammalian cell, need not be so limited. Other suitable cells include, but are not limited to, fungal cells and microbial cells. The cell can be in vitro or in vivo. Where the method is practiced in a therapeutic context (e.g., to ameliorate the effects of a pathological condition characterized by hyperproliferation of one or more cells) the Adocia-derived kinesin modulators are preferably administered in a therapeutically effective dose.

In still another embodiment, this invention provides methods of assaying a test compound for kinesin modulatory activity. The methods involve contacting a microtubule and a kinesin motor (e.g. a kinesin motor protein) with one of the Adocia-derived kinesin modulators described herein and detecting a change in kinesin motor activity resulting from the contacting. In a particularly preferred embodiment, the method is practiced with one of the kinesin modulators of Formulas I, and III–VI, more preferably with one of the kinesin modulators of Formulas I or III. The change in motor activity is preferably detected through a motility assay, a binding assay, an ADP release assay, or an assay for anti-mitotic activity. Typically the change in activity is evaluated with reference to a negative control (e.g., typically the same assay, but lacking a kinesin motor modulator) and/or with reference to a positive control (e.g., typically the same assay, with a different kinesin motor inhibitor, preferably one whose activity has previously been characterized).

This invention also provides Adocia-derived kinesin modulator kits. The kits typically include a container containing one or more of the Adocia-derived kinesin modulator described herein. The kits can optionally include a pharmacological excipient and/or a delivery vehicle. When the excipient and/or delivery vehicle are provided they may be provided combined with the kinesin motor inhibitor or in a separate container for combination at the time of use. The kit can also include instructional materials describing the use of the compounds in any of the methods described herein.

In still another embodiment, this invention provides methods of modulating kinesin motor activity. The methods involve contacting the kinesin motor with a small organic molecule that competitively inhibits the kinesin motor at a microtubule binding site. In a particularly preferred embodiment, the small organic molecule is an Adocia-derived kinesin modulator as described herein or a a small organic molecule is identified according to the methods described herein.

This invention also provides methods of identifying an agent that modulates the kinesin inhibitory activity of an Adocia kinesin inhibitor (e.g., on of the Adocia sulfates or Adocia derived kinesin inhibitors described herein). The methods involve contacting a microtubule and/or a kinesin motor and/or an Adocia kinesin inhibitor with a candidate agent; and detecting a change in the kinesin inhibitory activity of the Adocia kinesin inhibitor resulting from the contacting, wherein a change indicates the identification of an agent that modulates the kinesin inhibitory activity of the Adocia kinesin inhibitor.

Methods are also provided for identifying an agent that interferes with the binding of an Adocia kinesin inhibitor with a kinesin. These methods involve contacting a kinesin and an Adocia kinesin inhibitor (e.g. an adocia sulfate or an adocia derived kinesin modulator described herein) with a candidate agent; and detecting a decrease in the binding of the Adocia kinesin inhibitor with the kinesin resulting from said contacting, wherein a decrease indicates the identification of an agent that interferes with the binding of the Adocia kinesin inhibitor and the kinesin.

Also provided herein is a complex comprising an Adocia kinesin inhibitor and a kinesin.

Methods are also provided for modulating cellular growth in an organism (e.g., an animal or a plant). The methods preferably involve administering to the organism a composition comprising a pharmaceutically acceptable carrier any one or more of the compounds described herein (e.g. adocia sulfates or adocia-derived kinesin modulators) in a quantity sufficient to alter said cellular growth in an organism

DEFINITIONS

The term "molecular motor" refers to cytoskeletal molecule(s) that utilize chemical energy to produce mechanical force, and drive the motile properties of the cytoskeleton.

The terms "kinesin" and "kinesin superfamily" as used herein refer to a superfamily of eucaryotic motor proteins used to transport a large variety of cargoes along microtubule "tracks". Members of the kinesin superfamily are believed to be essential for mitotic and meiotic spindle organization, chromosome segregation, organelle and vesicle transport and many other processes that require microtubule based transport. The common feature of kinesins in the presence of a conserved ~350 amino acid motor domain which harbors the microtubule binding, ATP-hydrolyzing, and force transducing activities (see, e.g., Barton et al. (1996) *Proc. Natl. Acad. Sci. USA*, 93(5): 1735–1742, and Goldstein, (1993) *Annu. Rev. Genet.*, 27: 319–351).

The term "kinesin motor" is used to refer to one or more proteins involved in the transduction of chemical energy into mechanical energy. Kinesin is a force generating enzyme that hydrolyzes ATP to ADP and $P_i$ and uses the derived chemical energy to induce plus end directed movement along microtubules. This ubiquitous microtubule motor is thought to power anterograde organelle transport along microtubules. The term kinesin motor is intended to include kinesin related proteins inhibition of which inhibits kinesin motor activity. Kinesin heavy and light chains have been cloned and sequenced from a number of species including, but not limited to Drosophila (GenBank M24441), squid optic lobe (GenBank J05258), sea urchin and human (GenBank X65873), and rat (M75146, M75147, M75148), and the like (see, e.g., Yang et al. (1989) Cell 56: 879–889, Wright et al. (1991) *J. Cell. Biol.*, 113: 817–833, Navone et al. (1992) *J. Cell. Biol.*, 117:1263–1275, and Cyr et al. (1991) *Proc. Natl. Acad. Sci. USA*, 88: 10114–10118). In addition, the scientific literature is replete with detailed descriptions of kinesins (kinesin motors) and kinesin related proteins (see, e.g., Kreis and Vale (1993) *Guidebook to the Cytoskeletal and Motor Proteins,* Oxford University Press, Oxford, Vale (1990) *Curr. Opin. Cell. Biol,* 2: 15–22; Vale (1987) Ann. rev. Cell. Biol., 3: 347–378; and references therein).

The terms "kinesin motor inhibitor" or "inhibition of kinesin motor activity" refers to the decrease or elimination of kinesin/microtubule mediated transduction of chemical energy (e.g. as stored in ATP) into mechanical energy (e.g., force generation or movement). Such a decrease can be measured directly, e.g., as in a motility assay, or alternatively can be ascertained by the use of surrogate markers such as a decrease in the ATPase activity of the kinesin protein, and/or a decrease in the affinity and/or specificity of kinesin motor protein-microtubule binding interactions, and/or in a decrease in mitotic activity of a cell or cells. Conversely, a "kinesin motor agonist" or "upregulator of kinesin motor activity" refers to the increase of kinesin/microtubule mediated transduction of chemical energy (e.g. as stored in ATP) into mechanical energy (e.g. force generation or movement).

An "Adocia-derived compound" or "Adocia-derived kinesin modulator" as used herein refers to any of the kinesin modulators described herein (see, e.g. Formulas I, III, IV, V, and VI). It will be appreciated, that while the Adocia-derived compounds include natural products derived from sponges (or other marine organisms) the term also contemplates analogues of such compounds as described herein. The Adocia-derived compounds thus need not exist as natural products and may be chemically synthesized de novo.

The term "test compound" refers to a compound whose anti-kinesin motor activity it is desired to determine. Such test compounds may include virtually any molecule or mixture of molecules, alone or in a suitable carrier.

The term "detecting the binding" means assessing the amount of a given second component that binds to a given first component in the presence and absence of a test composition. This process generally involves the ability to assess the amount of the second component associated with a known fixed amount of the first component at selected intervals after contacting the first and second components. This may be accomplished e.g., by attaching to the second component a molecule or functional group that can be visualized or measured (e.g., a fluorescent moiety, a radio-active atom, a biotin that can be detected using labeled avidin) or by using ligands that specifically bind to the second component. The level of binding is preferably detected quantitatively. Binding, or a change in binding is indicated at the first detectable level. A change in binding, which can be an increase or a decrease, or presence versus absence, is preferably a change of at least about 10%, more preferably by at least about 20%, still more preferably by at least about 50%, still even more preferably by at least about 75%, even more preferably by at least about 150% or 200% and most preferably is a change of at least about 2 to about 10 fold (e.g., as compared to a control).

The phrase "detecting a change in the kinesin inhibitory activity of he Adocia kinesin inhibitor resulting from said contacting" refers to determining the presence or absence or quantifying the alteration in kinesin inhibitory activity caused by a particular candidate agent. assays for such determinations are further described herein. A change in activity, which can be an increase or a decrease, or presence versus absence, is preferably a change of at least about 10%, more preferably by at least about 20%, still more preferably by at least about 50%, still even more preferably by at least about 75%, even more preferably by at least about 150% or 200% and most preferably is a change of at least about 2 to about 10 fold (e.g., as compared to a control).

The phrase "detecting a change in kinesin motor activity resulting from said contacting" refers to determining the presence, absence or quantifying the alteration in kinesin motor activity caused by a particular composition (e.g. a test compound). The detecting can involve any one or more of a variety of assays for kinesin motor activity as described herein. A change in activity, which can be an increase or a decrease, or presence versus absence, is preferably a change of at least about 10%, more preferably by at least about 20%, still more preferably by at least about 50%, still even more preferably by at least about 75%, even more preferably by at least about 150% or 200% and most preferably is a change of at least about 2 to about 10 fold (e.g., as compared to a control).

The term "compound" as used herein refers to organic or inorganic molecules. The term includes, but is not limited to polypeptides, proteins, glycoproteins (e.g. antibodies), nucleic acids, oligonucleotides, and inorganic molecules.

The term "small organic molecule", as used herein, refers to a compound that is an organic molecules of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

A "bioagricultural compound" as used herein refers to a chemical or to a biological compound that has utility in agriculture or in environmental and functions to foster food or fiber crop or crop protection or yield improvement. For example, one such compound may serve as a herbicide to selectively control weeds, as a fungicide to control the spreading of plant diseases, as n insecticide to ward off and/or destroy insect, mite, and other arthropod pests. In addition, one such compound may demonstrate utility in seed treatment to improve the growth environment of a germinating seed, seedling, ro young plant as a plant regulator or activator. Other compounds can serve in environmental management such as, for example, forest management.

By "protein" herein is meant at least two covalently attached amino acids, which includes proteins, polypeptides, oligopeptides, and peptides. The protein may be made of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline, and norleucine are considered amino acids for the purposes of this invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

The terms "nucleic acid" or "oligonucleotide" or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) *Tetrahedron* 49(10):1925) and references therein; Letsinger (1970) *J. Org. Chem.* 35:3800; Sprinzl et al. (1977) *Eur. J. Biochem.* 81: 579; Letsinger et al. (1986) *Nucl. Acids Res.* 14: 3487; Sawai et al. (1984) *Chem. Lett.* 805, Letsinger et al. (1988) *J. Am. Chem. Soc.* 110: 4470; and Pauwels et al. (1986) *Chemica Scripta* 26: 141 9), phosphorothioate (Mag et al. (1991) *Nucleic Acids Res.* 19:1437; and U.S. Pat. No. 5,644,048), phosphorodithioate (Briu et al. (1989) *J. Am. Chem. Soc.* 111:2321, O-methylphophoroamidite linkages (see Eckstein, *Oligonucleotides and Analogues: A Practical Approach,* Oxford University Press), and peptide nucleic acid backbones and linkages (see Egholm (1992) *J. Am. Chem. Soc.* 114:1895; Meier et al. (1992) *Chem. Int. Ed. Engl.* 31: 1008; Nielsen (1993) *Nature,* 365: 566; Carlsson et al. (1996) *Nature* 380: 207). Other analog nucleic acids include those with positive backbones (Denpcy et al. (1995) *Proc. Natl. Acad. Sci. USA* 92: 6097; non-ionic backbones (U.S. Pat. Nos. 5,386,023, 5,637,684, 5,602,240, 5,216,141 and 4,469,863; Angew. (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghui and P. Dan Cook; Mesmaeker et al. (1994), *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, ASC Symposium Series 580, *Carbohydrate Modifications in Antisense Research,* Ed. Y. S. Sanghui and P. Dan Cook. Nucleic acids containing one or more carbocyclic sugars are also included within the definition of nucleic acids (see Jenkins et al. (1995), *Chem. Soc. Rev.* pp169–176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

The term "competitive inhibition" is used to refer to competitive inhibition in accord with the Michaelis-Menton model of enzyme kinetics. Competitive inhibition is recognized experimentally because the percent inhibition at a fixed inhibitor concentration is decreased by increasing the substrate concentration. At sufficiently high substrate concentration, $V_{max}$ can essentially be restored even in the presence of the inhibitor. Conversely, "non-competitive inhibition" refers to inhibition that is not reversed by increasing the substrate concentration.

The term "cell" is used to refer to any cell including, but not limited to mammalian, fungal, microbial and invertebrate cells. Preferred cells include tumor cells including, but not limited to, carcinomas, including breast, ovary, prostate, skin, and colon; brain cancers, including memingioma, glioma, oligodendroglioma, embryonic cancers; sarcomass; leukemias, and lymphomas. Preferred cells also include neurons. Particularly preferred neurons are those related to neurodegenerative diseases including Alzheimer's Disease, Parkinson's Disease, Huntington's Disease, Frontotemporal Dementias, and Amyotrophic Lateral Sclerosis. Preferred cells further include cells derived from the gastrointestinal system including esophagus, stomach, intestine, pancreas, liver, lung, heart, and vascular system as sell as cells from the central and peripheral nervous system, kidney, bladder, muscular system and the bone system.

"In vivo" refers to in the living body of an organism.

"In vitro" refers to outside the living body, such as, an artificial environment, for example, a test tube or a cell or tissue culture.

The term "modulate" as used herein refers to increaing or decreasing an activity of a molecule. Thus, for example, a kinesin motor modulator acts to increase or decrease (inhibit) kinesin motor activity.

BRIEF DESCRIPTION OF THE DRAWINGS

FIG. 4a shows that the apparent $K_m$ for microtubules depends linearly on adociasulfate concentration. The intercept with the x-axis gives a Ki value of 0.8 $\mu$M. b. Apparent Km for ATP does not depend on AS concentration, only $V_{max}$ is affected, FIG. 4a shows an example of the experimental trace. FIG. 4b shows that the magnitude of the burst of ADP release depends on adociasulfate concentration.

DETAILED DESCRIPTION

Figure 1A:
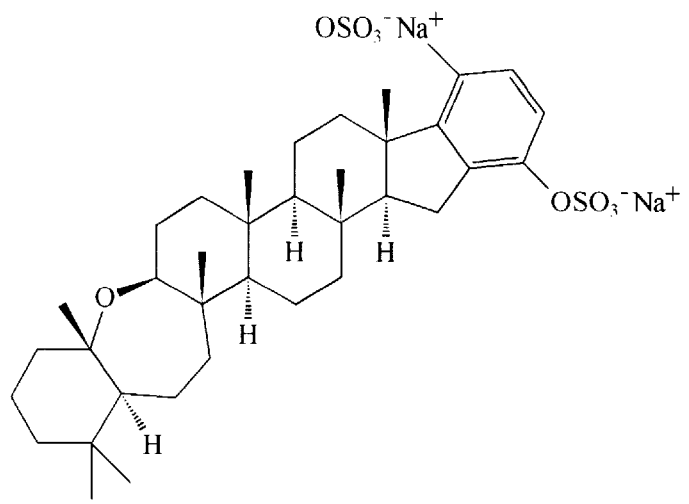
FIGS. 1a, 1b, and 1c show structures of preferred adociasulfates.

This invention provides a previously unknown class of specific enzyme modulators that act to modulate binding of kinesin motor proteins to microtubules and thereby alter kinesin motor activity. It is believed that prior to this invention, no small organic molecule modulators (that are not nucleotides or nucleotide analogues) of kinesin motors were known or even suspected to exist.

The kinesin motor modulators of this invention were initially derived from the sponge Adocia sp. and thus are referred to herein as Adocia compounds or Adocia-derived kinesin modulators (e.g. kinesin inhibitors). Specific preferred Adocia compounds are sulfates and consequently referred to herein as adociasulfates (AS).

I. Kinesin Motor Modulators.

A) Uses of kinesin motor modulators.

The kinesin motor modulators of this invention are useful in a wide variety of contexts. In particular, preferred modulators of his invention act to inhibit activity of kinesin mediated transport. The kinesins (members of the kinesin superfamily) are implicated in microtubule-mediated transport activities. As such they participate in a wide variety of activities including, but not limited to mitotic and meiotic spindle organization, chromosome segregation, organelle and vesicle transport and many others processes that require microtubule based transport.

Modulation (e.g. inhibition) of kinesin motors therefor has profound effect on cellular function acting, for example, to inhibit meiosis and/or mitosis, and consequently inhibiting cellular growth and/or proliferation, e.g. in vitro or in humans and other non-human animals. As powerful antimitotics or anti-meiotics, the kinesin inhibitors of this invention have a wide variety of uses, particularly in the treatment (e.g., amelioration) of, e.g. human and veterinary, pathological conditions characterized by abnormal cell proliferation. Such conditions include, but are not limited to: fungal infections, abnormal stimulation of endothelial cells (e.g., atherosclerosis), solid tumors and tumor metastasis, benign tumors, for example, hemangiomas, acoustic neuromas, neurofibromas, trachomas, and pyogenic granulomas, vascular malfunctions (e.g., arterio-venous malformations), abnormal wound healing, inflammatory and immune disorders, Bechet's disease, gout or gouty arthritis, abnormal angiogenesis accompanying: rheumatoid arthritis, psoriasis, diabetic retinopathy, and other ocular angiogenic diseases such as retinopathy of prematurity (retrolental fibroplasic), macular degeneration, corneal overgrowth, corneal graft rejection, neuroscular glaucoma, Oster Webber syndrome, and the like. In addition, it is expected the kinesin motor inhibitors of this invention are useful in the treatment/mitigation of a number of neurodegenerative disorders.

The kinesin motor modulators of this invention also find use in the prevention and treatment of plant diseases caused by, for example, fungi (e.g., *Plasmodiophora brassicae* (club foot of crucifers), *Synchytrium endobioticum* (potato black wart disease), *Plasmopara viticola* (downy mildew of grape), *Phytophthora infestans* (late blight of pato and tomato), etc), nematodes, insects, mites, or other arthropod pests, or parasitic seed plants (e.g., witchweed (*Striga asiatica*), dwarf mistletoe (Arceuthobium), etc.). Accordingly, the kinesin motor modulators find use in bioagricultural and environmental management settings as herbicides, fungicides, pesticides, or insecticides. In a preferred embodiment, the kinesin motor modulator is administered to plants with a bioagriculturally acceptable carrier or exipient.

The kinesin motor modulators of this invention also have a variety of in vitro uses as well. For example, they can be used to freeze cells in a particular stage of the cell cycle for a variety of purposes (e.g., in the preparation of samples for of histological examination), in the isolation of nucleic acids from a particular stage of the cell cycle, and so forth.

The kinesin motor modulators of the invention also find use in the diagnosis of human and veterinary diseases, conditions, or pathologies associated with abnormal kinesin superfamily function, for example, disease states or conditions associated with hypersensitivity or resistance to kinesin motor modulators.

The kinesin motor modulators of this invention show unique specificity of kinesin motor/microtubule interactions. They therefor provide novel lead compounds for the development of highly specific inhibitors or upregulators for kinesin families and subfamilies, thus allowing for precise chemical intervention. In addition, the ability of the Adocia compounds of this invention to mimic microtubules in kinesin motor binding allow the creation of artificial kinesin tracks for use in various kinesin microtubule assays (e.g., motility assays). Because of their ability to modulate the activity of kinesin motors (the conversion of chemical energy to mechanical activity) the kinesin motor modulators of this invention are useful for the production of nano-switches and other nano-devices (e.g., nanometer scale miro machines).

B) Preferred Kinesin Motor Modulators.

In a preferred embodiment, this invention provides Adocia-derived kinesin motor modulators characterized by a compound according to Formula (I)

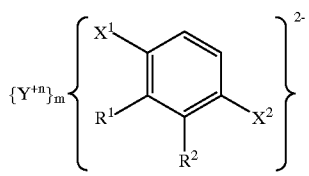

in which $R^1$ and $R^2$ are either independent monovalent moieties independently selected from the group of H, hemiterpenes, terpene monomers and terpene oligomers such that at least one of $R^1$ and $R^2$ is not H, or $R^1$ and $R^2$ are combined to form a single divalent terpene moiety selected from the group consisting of hemiterpenes, terpene monomers and terpene oligomers; $X^1$ and $X^2$ are the same or different and are anionic derivatives of an organic group, an inorganic group or a group which is a combination of organic and inorganic groups; $Y^{+n}$ is an organic or inorganic cation; m is either 1 or 2; and n is either 1 or 2.

Terpenes are characterized as being made up of units of isoprene in a head-to-tail orientation. The terpenes are further classified by the number of isoprene units in their carbon skeletons, as shown in Table 1.

TABLE 1

| Terpene classification | | |
|---|---|---|
| Isoprene Units | Carbon Atoms | Classification |
| 1 | 5 | hemiterpene |
| 2 | 10 | monoterpene |
| 3 | 15 | sesquiterpene |

TABLE 1-continued

| Terpene classification | | |
|---|---|---|
| Isoprene Units | Carbon Atoms | Classification |
| 4 | 20 | diterpene |
| 5 | 25 | sesterterpene |
| 6 | 30 | triterpene |
| 8 | 40 | tetraterpene |
| >8 | >40 | polyterpene |

As used herein, the general term "terpenoid" encompasses hemiterpenes, terpene monomers, terpene oligomers and meroterpenes. "Terpene monomers" refers to derivatized or underivatized terpenes consisting of ten carbon atoms. "Terpene oligomers" refers to derivatized or underivatized terpenes having more than ten carbons. "Meroterpenes" refers to terpenes that are directly attached to any aromatic ring. Terpenoids which are named with a prefix (e.g., hemiterpenes, triterpenes, etc.) include both derivatized and underivatized analogs of these terpenoids.

In a preferred embodiment, the terpendoids are oligomeric. In a further preferred embodiment, the terpene oligomers are members selected from the group of diterpenes, sesquiterpenes, triterpenes, sesterterpenes and triterpenes. In a still further preferred embodiment, the terpenoid is a triterpene.

Derivatized terpenes include, for example, terpene alcohols, aldehydes, ketones, ethers and esters. Each of these terms is used in its normal art-accepted manner. In a presently preferred embodiment, the invention provides compounds which are terpene alcohols. In another presently preferred embodiment, the invention provides compounds which are terpene ethers. In still a further preferred embodiment, the ethers are cyclic ethers.

The compounds of the invention can be linear terpenes or terpenes which include within their structural framework one or more rings. In a preferred embodiment, the terpenes are polycyclic, preferably having more than two rings and more preferably having more than four rings. A ring can be saturated, can contain unsaturation or can be aromatic. A ring can have from four to seven members and can consist of only carbon atoms or carbon atoms in conjunction with heteroatoms. Presently preferred heteroatoms include nitrogen, oxygen and sulfur. In a preferred embodiment, the rings are composed entirely of carbon atoms. In another preferred embodiment, a ring contains one or more oxygen heteroatoms. In a still further preferred embodiment, a ring contains a single oxygen atom.

A compound of the invention can have either one or two terpenoids attached to the benzene nucleus. When two terpenoids are present they can be identical or different. Both terpenoids can contain one or more cyclic structures within their framework, both can be linear or one can be linear and the other can contain one or more cyclic structures within its framework. In this embodiment, a terpenoid can be attached to the benzene nucleus as a monovalent moiety or it can be fused to the benzene nucleus as a divalent moiety. In another preferred embodiment, the compounds consist of one terpenoid attached to the benzene nucleus. In a further preferred embodiment, the terpenoid has at least one cyclic structure within its framework. In a preferred embodiment, the terpenoid is fused to the benzene nucleus.

The benzene nucleus is functionalized with two anionic groups. The anionic groups can be either the same or different and they are derived from acidic organic groups, acidic inorganic groups or groups which contain an acidic inorganic group tethered to an organic group.

Acidic organic groups are primarily derived from carboxylic acids and thiocarboxylic acids. The carboxylic acids are attached to the benzene ring directly or through a hydrocarbon chain of between one and five carbon atoms. In preferred embodiments, the organic acid is attached directly to the benzene nucleus (e.g., phenylformic or phenylthioformic acid) or through a one carbon spacer (e.g., phenylacetic or phenylthioacetic acid).

When a hydrocarbon chain is present, this chain can be substituted with groups which have the effect of modulating the acidity of the acid. Thus, electronegative groups (e.g., F, Cl, Br, $NO_2$, etc.) attached to the hydrocarbon chain increase the acidity of the attached acidic group. In an opposite manner, electropositive groups (e.g., alkyl, alkenyl) decrease the acidity. the hydrocarbon chain can be attached to the benzene nucleus through a carbon atom or can be attached via a heteroatom such as oxygen (e.g., glycolic acid).

Inorganic acidic groups are derived from inorganic acids including, but not limited to, phosphoric acid, phosphonic acid, phosphinic acid, boronic acid, sulfuric acid, sulfonic acid, arsonic acid and the like. The acid is bound to the benzene nucleus by either the central atom of the acid, or through an oxygen atom to form an "inorganic ester." Examples of these two modes of attachment include, for example, phenylphosphinic acid and phenyl phosphate, respectively. In a presently preferred embodiment, the acid is a sulfur containing acid. In an further preferred embodiment the acid is bound to the benzene nucleus via an oxygen atom. In yet another preferred embodiment, the acid is derived from sulfuric acid.

Acids which are derived from species consisting of organic radicals and inorganic acids include, for example, alkyl sulfuric acids, alkyl phosphoric acids, alkyl phosphinic acids and the like.

The cations which are associated with the anionic groups are either organic or inorganic cations. The cations can have either a $^{+}1$ or $^{+}2$ charge. When a cation with a $^{+}1$ charge used, two cations will be associated with the molecule. When a $^{+}2$ cation is used, only one cation is necessary.

Inorganic cations include ions of Groups 1–12. Preferred inorganic cations include, but are not limited to, the cations of Li, Na, K, Cs, Mg, Ca, Mn, Fe, Co, Ni, Cu and Zn. Further preferred inorganic cations are the cations of Li, Na and K.

Organic cations include, for example, tetraalkyl ammonium salts. The ammonium salts of the present invention are monovalent (e.g., $R_4N^+Y^-$) or divalent as illustrated by Formula (II).

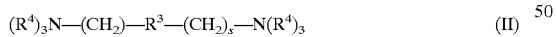

$$(R^4)_3N-(CH_2)_t-R^3-(CH_2)_s-N(R^4)_3 \quad (II)$$

in which $R^3$ is a $C_1$ to $C_{10}$ aryl, substituted aryl, alkyl or substituted alkyl group and $R^4$ is lower alkyl or substituted lower alkyl. The letters s and t represent integers from 1 to 5 and can be the same or different. When the ammonium salt is monovalent, the alkyl group the characteristics of the nitrogen substituents will be generally the same as those discussed in the context of $R^4$.

A named R group will generally have the structure which is recognized in the art as corresponding to R groups having that name. For the purposes of illustration, representative R groups as enumerated above are defined herein. These definitions are intended to supplement and illustrate, not preclude, the definitions known to those of skill in the art.

The term "alkyl" is used herein to refer to a branched or unbranched, saturated or unsaturated, monovalent hydrocarbon radical having from 1–10 carbons and preferably, from 1–6 carbons. When the alkyl group has from 1–6 carbon atoms, it is referred to as a "lower alkyl." Suitable alkyl radicals include, for example, methyl, ethyl, n-propyl, i-propyl, 2-propenyl (or allyl), n-butyl, t-butyl, i-butyl (or 2-methylpropyl), etc.

The term "substituted alkyl" refers to alkyl as just described including one or more functional groups such as lower alkyl, aryl, acyl, halogen (i.e., alkylhalos, e.g., $CF_3$), hydroxy, amino, alkoxy, alkylamino, acylamino, acyloxy, aryloxy, aryloxyalkyl, mercapto, both saturated and unsaturated cyclic hydrocarbons, heterocycles and the like. These groups may be attached to any carbon of the alkyl moiety.

The term "aryl" is used herein to refer to an aromatic substituent which may be a single aromatic ring or multiple aromatic rings which are fused together, linked covalently, or linked to a common group such as a methylene or ethylene moiety. The common linking group may also be a carbonyl as in benzophenone. The aromatic ring(s) may include phenyl, naphthyl, biphenyl, diphenylmethyl and benzophenone among others.

"Substituted aryl" refers to aryl as just described including one or more functional groups such as lower alkyl, acyl, halogen, alkylhalos (e.g., $CF_3$), hydroxy, amino, alkoxy, alkylamino, acylamino, acyloxy, mercapto and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone.

In a presently preferred embodiment, the organic cation is a compound according to Formula (II). In a further preferred embodiment, $R^3$ is phenyl and $R^4$ is lower alkyl. In another preferred embodiment, both $R^3$ and $R^4$ are lower alkyl. In these embodiments, s and t are preferably between 1 and 3, more preferably 1.

In a further embodiment, the invention provides for compounds having a structure according to Formula (III):

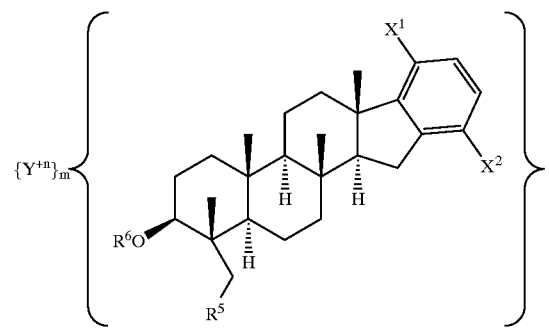

in which $R^5$ and $R^6$ are either independent monovalent moieties independently selected from the group consisting of H, hemiterpenes, terpene monomers and terpene oligomers such that at least on of $R^5$ and $R^6$ is not H, or $R^5$ and $R^6$ are combined to form a single divalent moiety selected from the group consisting of hemiterpenes, terpene monomers and terpene oligomers. In a presently preferred embodiment, $R^5$ and $R^6$ are combined to form a seven-membered cyclic ether. In another preferred embodiment, $R^5$ is a terpenoid and $R^6$ is H.

In another embodiment, the present invention provides for adociasulfate compounds having a structure according to Formula (IV).

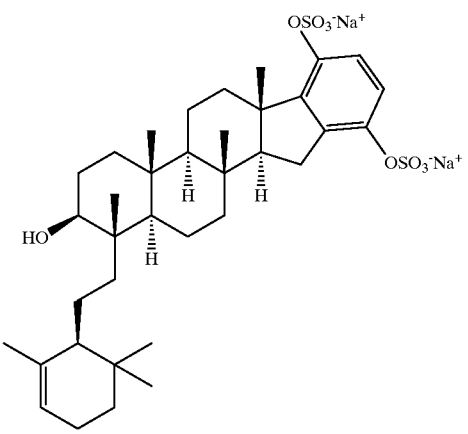

(IV)

In an additional embodiment, the invention provides an adociasulfate compound having a structure according to Formula (V).

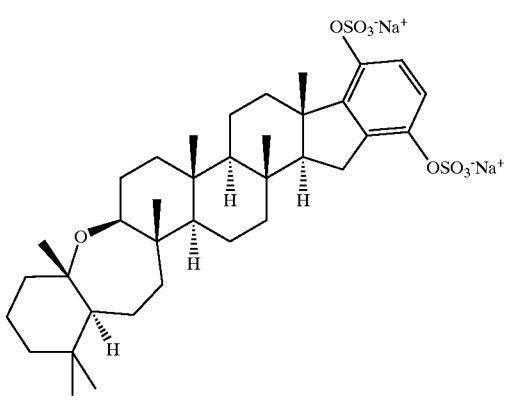

(V)

In a still further embodiment, the present invention provides an adociasulfate compound having a structure according to Formula (VI).

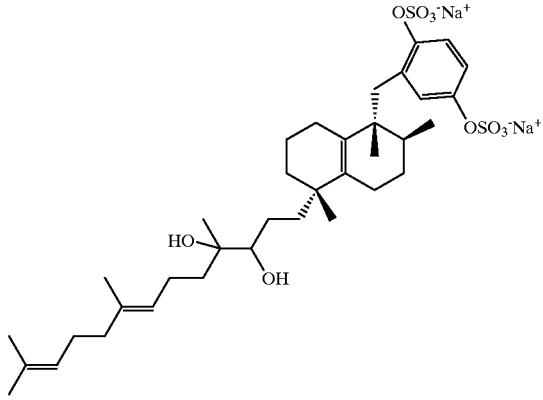

(VI)

II. Isolation and/or synthesis of Adocia-derived kinesin motor modulators.

The Adocia-derived kinesin motor modulators of this invention can be created de novo according to standard methods of chemical synthesis. Alternatively, where the modulators are natural products, they can be isolated from the organisms in which they are produced according to standard methods.

A) Chemical synthesis of Adocia compounds.

Figure 6:
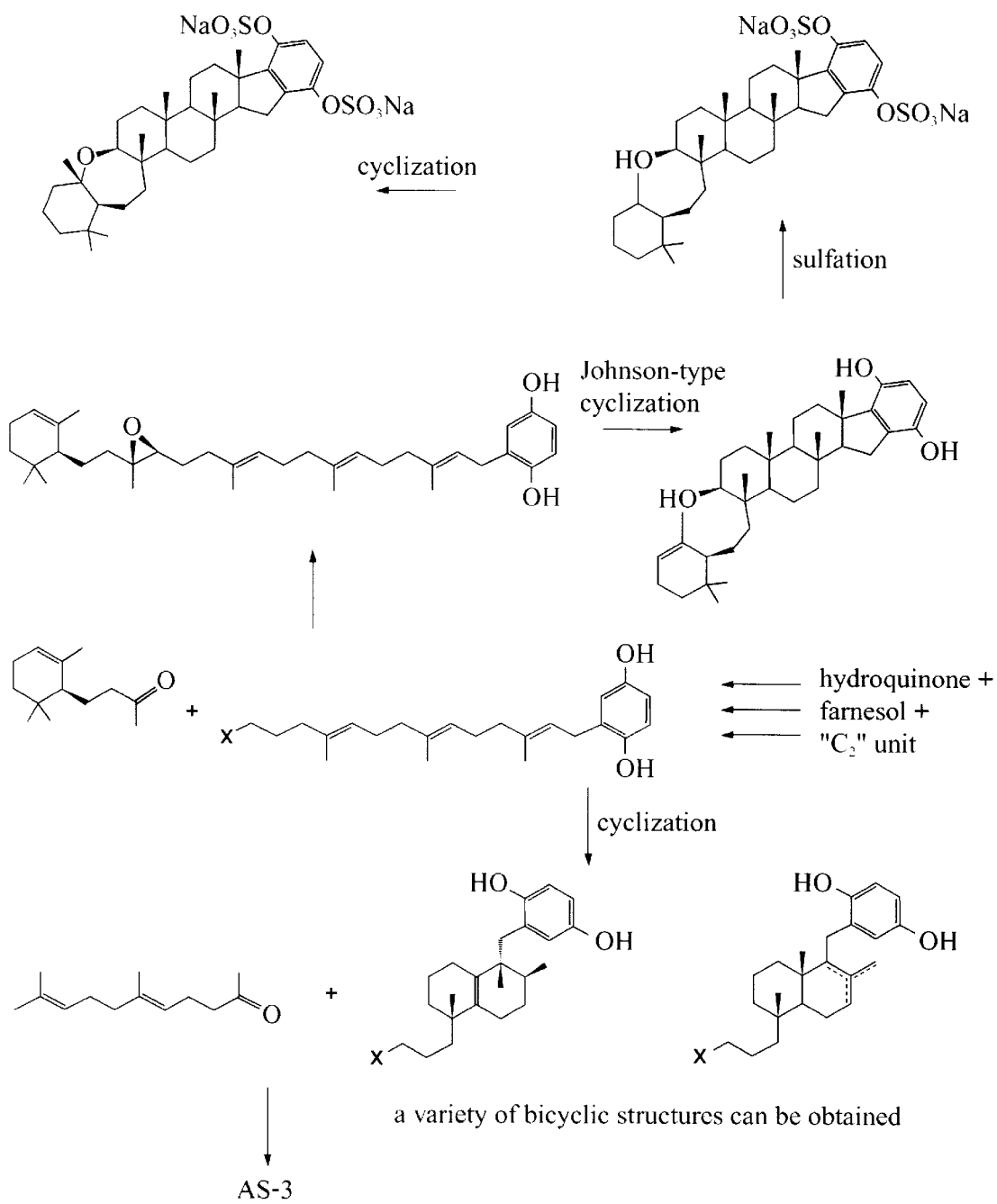
FIG. 6 illustrates synthetic schemes for the production of Adocia-derived kinesin inhibitors of this invention.

Using the structures provided herein, de novo synthesis of the compounds of this invention can be achieved using standard methods well known to those of ordinary skill in the art. In addition, the compounds of FIGS. 1a, 1b, and 1c, which can be isolated from sponges, as described below, provide convenient substrates which can be modified to produce the other compounds described herein. De novo synthesis of terpenoids and/or modification of terpenoids is routine and well known to those of skill in the art (see, e.g., U.S. Pat. No. 5,596,127 Process for the continuous preparation of terpene esters; U.S. Pat. No. 5,399,724 Acyclic terpene compound; U.S. Pat. No. 5,202,460 Terpene derivatives, their preparation and their use; U.S. Pat. No. 5,073,659 Process for the preparation of terpenes; U.S. Pat. No. 4,623,747 Terpene diesters and process for preparing the same; U.S. Pat. No. 4,137,257 Terpene hydroxysulfonic acids and corresponding hydroxysulfonate salts; U.S. Pat. No. 4,029,649 Terpene aryl esters, and Ho, (1988) *Carbocycle construction in terpene synthesis,"* New York; Kaufman et al. (1995) *J. Med. Chem.* 38: 1437–45; Gould, (1995) *J. Cell. Biochem. Suppl.* 22:139–144; and Szirmai et al.(1995) *Bioorg. Med. Chem.* 3:899–906. Typical synthesis schemes are provide in FIG. 6.

B) Purification of Adocia compounds.

The compounds of the present invention can also be isolated from natural sources. The fields of natural products isolation and terpene synthesis are well developed. Methods of purifying terpenoids of natural origin and elucidating their structures are known to those of skill in the art.

In a preferred embodiment, the Adocia-derived kinesin motor modulators are purified according to the method described in Example 1.

III. Assay of Adocia-derived kinesin motor modulators for activity.

It will be appreciated that the different Adocia compounds of this invention may exhibit different levels of kinesin motor modulatory activity. Consequently, it is desirable to identify those Adocia-derived kinesin modulators of this invention that exhibit the highest level of activity and/or those that show various optimum levels of activity. Thus, in one embodiment, this invention provides methods of assaying (screening) the Adocia-derived kinesin motor modulators for activity. The screening may involve detection of presence or absence of kinesin motor modulatory activity or quantification of such activity. In a preferred embodiment, such quantification is relative to a control lacking any modulator and/or to a reference kinesin modulator compound. The reference compound may be an modulator of this invention or a different modulator. Thus, for example, in a preferred embodiment, the screened compound will be scored as a strong inhibitor if it has inhibitory activity equal to or greater than the compounds of Formulas IV, V, or VI, , more preferably the compound of formula IV, in a motility, binding, ATPase, or anti-mitotic assay (e.g. the assays described in the Examples herein). Particularly preferred screened compounds exceed the inhibitory activity of the compounds of Formulas IV, V, or VI, most preferably Formula IV by a factor of at least 2, more preferably by a factor of at least 5, and most preferably by a factor of at least 10.

While many assays for kinesin modulation are known to those of ordinary skill in the art, particularly preferred assays include motility assays, binding assays, and assays for anti-mitotic activity.

A) Motility assays.

Because the microtubule/kinesin motor system transduces chemical energy into force generation and molecular movement, motility assays provide a convenient means for assaying for modulators of the kinesin motor proteins; stronger motor modulators producing a greater increase or decrease in motility or having a particular effect at lower concentration. Generally motility assays involve immobilizing one component of the system (e.g, the kinesin motor or the microtubule) and then detecting movement, or inhibition thereof, of the other component. Thus, for example, in a preferred embodiment, the microtubule will be immobilized (e.g., attached to a solid substrate) and the movement of the kinesin motor molecule(s) will be visually detected. Typically the molecule that is to be detected is labeled (e.g., with a fluorescent label) to facilitate detection.

Methods of performing motility assays are well known to those of skill in the art (see, e.g., Hall, et. al (1996), *Biophys. J.*, 71: 3467–3476, Turner et al., 1996, *Anal. Biochem.* 242 (1): 20–5; Gittes et al., 1996, *Biophys. J* 70 (1): 418–29; Shirakawa et al., 1995, *J. Exp. Biol.* 198: 1809–15; Winkelmann et al., 1995, *Biophys. J.* 68: 2444–53; Winkelmann et al., 1995, *Biophys. J.* 68: 72S, and the like). In addition, a suitable motility assay is described in Example 2.

B) Binding assays.

In addition to, or in alternative to, motility assays, binding assays can also be used to assay (detect and/or quantify) modulation of kinesin motor proteins. In binding assays, the ability of the putative kinesin motor modulator to inhibit or increase binding of the kinesin motor protein(s) to microtubules are assayed.

There are a wide variety of formats for binding assays. In one embodiment, the microtubule or the motor protein is attached to a solid support. The corresponding motor protein or microtubule is then contacted to the support in the presence of the modulator to be screened and the amount of bound motor protein or microtubule is then detected and/or quantified (for suitable binding assay formats, see copending application U.S. Ser. No. 60/057,895, filed on Sep. 4, 1997.

Solution phase binding assays are also known to those of skill in the art. For example, in one embodiment, the binding assay is a kinesin-microtubule cosedimentation assay (Example 1). In this assay, (pelleting) assay, kinesin binds to microtubules in the presence of AMP-PNP, a non-hydrolysable analogue of ATP, and sediments to the bottom of the tube after centrifugation to form a pellet. The non-hydrolysable ATP analogue permits kinesin-microtubule binding, but not release. Meanwhile, unbound kinesin remains in the supernatant. The negative control (lacking modulator) has saturating amounts of kinesin bound to the microtubules. In the presence of kinesin motor inhibitors such as the adociasulfates described herein, most of the motor remains in the supernatant.

In one preferred embodiment, the assay, involves

1) Adding PEM80 and DMSO(control)/modulator to tube and mix thoroughly;
2) Adding other components: Kinesin, microtubules, and 2 mM MgAMP-PNP;
3) Centrifuging the tubes (e.g., in Beckman 42.2 rotor at 25,000 g, 30 minutes, 20° C.);
4) Analyzing the supernatant and pellets on 10% SDS-PAGE.

Methods of performing kinesin motor-microtubule binding assays can be found in copending application U.S. Ser. No. 60/057,895 filed on Sep. 4, 1997. For a general description of different formats for protein binding assays, including competitive binding assays and direct binding assays, see Stites and A. Terr (1991) *Basic and Clinical Immunology,* 7th Edition; Maggio (1980) *Enzyme Immunoassay,* CRC Press, Boca Raton, Fla.; and Tijssen (1985) *Practice and Theory of Enzyme Immunoassays,* in *Laboratory Techniques in Biochemistry and Molecular Biology,* Elsevier Science Publishers, B.V. Amsterdam.

C) ATPase assay.

Kinesin motors are effective ATPases hydrolyzing ATP to ADP to provide energy for force generation. By examining ADP release from kinesin in the presence of varying concentrations of kinesin motor modulator (e.g., adociasulfate), the activity of the kinesin motor modulator can be quantified. One such ADP release assay is described in Example 1. In one preferred embodiment, the ATPase activity assay utilizes 0.3 M PCA (perchloric acid) and malachite green reagent (8.27 mM sodium molybdate II, 0.33 mM malachite green oxalate, and 0.8 mM Triton X-100). To perform the assay, 10 $\mu$L of reaction is quenched in 90 $\mu$l of cold 0.3 M PCA. Phosphate standards are used so data can be converted to mM inorganic phosphate released.

When all reactions and standards have been quenched in PCA, 100 $\mu$l of malachite green reagent is added to the to relevant wells in e.g., a microtiter plate. The mixture is developed for 10–15 minutes and the plate is read at an absorbance of 650 nm. If phosphate standards were used, absorbance readings can be converted to mM Pi and plotted over time.

D) Mitotic activity assays.

Assays for mitotic activity typically involve contacting a cell (in vitro or in vivo) the test compound and assaying its effect on the ability of the cell proliferate. Alternatively, a mass of cells can be contacted with the compound and the rate of growth of the mass can be measured.

1) Anti-mitotic activity in situ.

In one preferred embodiment, anti-mitotic activity of the kinesin motor modulator of this invention can be assayed in Situ by testing the ability of the modulator to alter the proliferation of new blood vessel cells (angiogenesis). Such proliferation assays are well known to those of skill in the art. One suitable assay is the chick embryo chorioallantoic membrane (CAM) assay described by Crum et al. (1985) *Science* 230:1375. See also, U.S. Pat. No. 5,001,116, which describes the CAM assay.

Briefly, fertilized chick embryos are removed from their shell on day 3 or 4, and a methylcellulose disc containing a particular amount (e.g., 100 mg) of the compound to be screened is implanted on the chorioallantoic membrane. The embryos are examined 48 hours later and, if a clear avascular zone appears around the methylcellulose disc, the diameter of that zone is measured. Using this assay, a disk of the Adocia-derived compound of this invention is expected to alter cell mitosis and the growth of new blood vessels after 48 hours. Inhibition of normal blood vessel growth indicates that the Adocia-derived kinesin modulator is an inhibitor of cell mitosis and angiogenesis.

2) Anti-mitotic activity in vitro.

In vitro assays for anti-mitotic activity are also well known to those of skill in the art. Typically such assays involve contacting a cell (e.g. a cell in culture) with the compound that is to be assayed and determining the effect on cellular proliferation. The cell can be one that proliferates at a normal (e.g. endogenous) rate, or, alternatively, can be a cell in which hyperproliferation has been stimulated. Measurement of cellular proliferation can be direct (e.g., a cell count) or indirect, e.g., through a surrogate marker such as rate of incorporation of a labeled amino acid. Such assays are standard and well known to those of skill in the art. Descriptions of assays for anti-mitotic activity are found, for example, in U.S. Pat. Nos. 5,620,687 and 5,443,962.

3) Anti-mitotic activity in vivo.

In vivo assays for anti-mitotic activity are also well known to those of skill in the art. Typically these assays involve administering the test compound to a subject organism and then evaluating the effect of the compound on a target tissue or organ. Preferred organisms are those in which a hyperproliferative tissue or organ is manifest. Such organisms are well known to those of skill in the art and include, for example, standard tumor models (e.g., tumors introduced into nude mice) (see, e.g., Sharkey et al. (1990) Cancer Res. 50: 828s–834s). Organisms having other natural or induced pathological conditions characterized by abnormal cell proliferation are also suitable.

E) Identifying specific modulators of microtubule binding.

As explained above, it was a discovery of this invention that small organic molecules can specifically modulat kinesin activity by targeting the kinesin motor domain and mimicking the activity a microtubule. The molecules thus act as competitive inhibitors for microtubule binding. This is a previously unknown mechanism of kinesin (or other motor, e.g., myosin or dynein) inhibition. Thus, in one embodiment, this invention provides methods of identifying kinesin inhibitors that specifically block the microtubule binding site. It is also expected that some small organic molecules will facilitate interactions at the microtubule binding site and similar assays can be used to identify such enhancers of kinesin motor activity.

Such specific blockers are characterized by the fact that they can be competitively inhibited by, or competitively inhibit, binders of the microtubule binding site, but not binders at the ATPase site. In one embodiment, this invention therefor provides methods of identifying compounds, especially small organic molecules, that change kinesin motor activity by partially or completely blocking the microtubule binding site. The methods involve screening the "test" compound's ability to competitively inhibit binding of a moiety (e.g., ATP or an ATP analogue) at the ATPase site and screening the same compound's ability to competitively inhibit binding of a moiety (e.g.., a microtubule) at the microtubule binding at the microtubule binding site.

A kinesin modulator that shows competitive inhibition at the microtubule binding site, but not at the ATPase site is identified as an inhibitor that specifically binds to the microtubule site.

Methods of identifying competitive inhibition are well known to those of skill in the art. Briefly, in the classical Michaelis-Menton model of enzyme kinetics, competitive inhibition is easily recognized experimentally because the percent inhibition at a fixed inhibitor concentration is decreased by increasing the substrate concentration. Thus, where the compound competitively inhibits binding at the microtubule binding site, increasing the microtubule concentration at a fixed concentration of test compound can restore the original (inhibitor-free) maximal rate of reaction ($V_{max}$). Conversely, where competition is non-competitive increasing the substrate concentration will not restore the maximal rate of reaction (Vmax). Assays for specific inhibition at the microtubule binding site are illustrated in example 1. For a detailed discussion of analysis of reaction kinetics to recognize competitive, noncompetitive and uncompetitive inhibition, see, e.g., Lehninger (1975) Biochemistry Worth Pub., Inc. New York, N.Y.

Included herein are assays that identify agents which modulate the interaction of Adocia kinesin modulators with kinesins. In the case where an agent is identified as altering (e.g., interfering with) the binding of the inhibitor with the kinesin, that agent can be subjected to further screening to determine its kinesin modulatory activity in accordance with the assays provided herein. It is understood that microtubules or their components are excluded as interfering agents. Similarly, identified modulators of the inhibitory activity of the Adocia kinesin inhibitors can be subjected to further screening. In particular, screens can be performed to determine whether the modulators work in conjunction or competitively with the Adocia kinesin inhibitors. Those modulators which function competitively are then further assayed independently to determine their activity.

F) High throughput screening.

Conventionally, new chemical entities with useful properties are generated by identifying a chemical compound (called a "lead compound") with some desirable property or activity, creating variants of the lead compound, and evaluating the property and activity of those variant compounds. However, the current trend is to shorten the time scale for all aspects of drug discovery. Because of the ability to test large numbers quickly and efficiently, high throughput screening (HTS) methods are replacing conventional lead compound identification methods.

In one preferred embodiment, high throughput screening methods involve providing a library containing a large number of potential therapeutic compounds (candidate compounds). Such "combinatorial chemical libraries" are then screened in one or more assays, as described herein, to identify those library members particular chemical species or subclasses) that display a desired characteristic activity. The compounds thus identified can serve as conventional "lead compounds" or can themselves be used as potential or actual therapeutics. In a preferred embodiment, combinatorial chemical libraries are provided containing the Adocia-derived compounds described herein.

Devices for the preparation of combinatorial libraries are commercially available (see, e.g., 357 MPS, 390 MPS, Advanced Chem Tech, Louisville, Kent., Symphony, Rainin, Woburn, Mass., 433A Applied Biosystems, Foster City, Calif., 9050 Plus, Millipore, Bedford, Mass.).

A number of well known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

Any of the assays for anti-kinesin motor activity described herein are amenable to high throughput screening. As described above, the adocia-derived compounds are preferably screened for anti-kinesin motor activity in binding assays, motility assays, or assays for anti-mitotic activity.

High throughput systems for such screening are well known to those of skill in the art. Thus, for example, U.S.

Pat. No. 5,559,410 discloses high throughput screening methods for protein binding, while U.S. Pat. Nos. 5,576,220 and 5,541,061 disclose high throughput methods of screening for ligand/antibody binding.

In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configuarable systems provide high throughput and rapid start up as well as a high degree of flexibility and customization. The manufacturers of such systems provide detailed protocols the various high throughput. Thus, for example, Zymark Corp. provides technical bulletins describing screening systems for detecting the modulation of gene transcription, ligand binding, and the like.

IV. Modulation of kinesin motor activity of cells.

In one embodiment, this invention provides for methods of modulating kinesin motor activity of cells. It will be appreciated that were the cells are cells that hyperproliferate in vivo in any of the pathological conditions described above, the kinesin motor modulators of this invention can act as potent anti-mitotic therapeutic agents. However, it will also be appreciated that therapeutic activity is not required for all uses of the compounds of this invention. The compounds can act as significant lead compounds for the development of therapeutics. Alternatively, the compounds can be used to inhibit growth or proliferation of cells in vitro, to prevent contamination of biological samples and the like with pathogenic organisms (e.g., fungi) or to facilitate processing of the biological materials (e.g., in histological preparations).

A) Indications.

As indicated above, the kinesin motor modulators of this invention can be used to mitigate a variety of pathological conditions (e.g., in humans and animals)characterized by abnormal cell mitosis. Such diseases include, but are not limited to: abnormal stimulation of endothelial cells (e.g., atherosclerosis), solid tumors and tumor metastasis, benign tumors, for example, hemangiomas, acoustic neuromas, neurofibromas, trachomas, and pyogenic granulomas, vascular malfunctions, abnormal wound healing, inflammatory and immune disorders, Bechet's disease, gout or gouty arthritis, abnormal angiogenesis accompanying: rheumatoid arthritis, psoriasis, diabetic retinopathy, and other ocular angiogenic diseases such as, macular degeneration, corneal graft rejection, corneal overgrowth, neuroscular glacoma, Oster Webber syndrome, and the like.

The kinesin motor modulators of this invention can also be used to mitigate variety plant diseases caused by abnormal cell division, or intracellular transport, or parasitic infections caused by, for example, microorganisms, nematodes, insects, and parasitic plants.

In addition, the kinesin motor modulators can be administered in vivo for non-therapeutic purposes (e.g., to rapidly kill and fix cells for histological procedures), to elucidate the role of kinesin motors in early development, and so forth. These applications are not intended to be limiting, but rather indicative of the multiplicity of different uses for the kinesin motor modulators of this invention. Other uses of the kinesin motors will be apparent to those of skill in the art.

B) Compositions for in vivo administration.

The kinesin motor modulators of this invention can be administered orally, transdermally, by subcutaneous or other (e.g., intravenous injection, intra-arterial injection, or direct injection into the target tissue) injection, intravenously, topically, parenterally, transdermally, or rectally. In addition, the kinesin motor modulators may be incorporated into biodegradable polymers (or other reservoir) allowing for sustained release, the polymers being implanted in the vicinity of where delivery is desired, for example, at the site of a tumor. The biodegradable polymers and their use are described in detail in Brem et al., (1991) *J. Neurosurg.* 74:441–446. The form in which the kinesin motor modulator will be administered (e.g., powder, tablet, capsule, solution, emulsion) will depend on the route by which it is administered. The quantity of the drug to be administered will be determined on an individual basis, and will be based at least in part on consideration of the individual's size, the severity of the symptoms to be treated and the result sought as described above.

The kinesin motor modulator compounds are preferably administered in the form of an acid addition salt thereof, sequentially or simultaneously with a pharmaceutically-acceptable carrier or diluent, especially and preferably in the form of a pharmaceutical composition thereof, whether by the topical, oral, rectal, or parenteral (including subcutaneous) route, in an effective amount.

The compositions for administration will commonly comprise a solution of the kinesin motor modulator dissolved or suspended in a pharmaceutically acceptable carrier. A variety of carriers can be used, e.g., buffered saline containing suitable emulsifiers, and the like. Methods of producing liposomes and complexing or encapsulating compounds therein are well known to those of skill in the art (see, e.g., Debs and Zhu (1993) WO 93/24640; Mannino and Gould-Fogerite (1988) *BioTechniques* 6(7): 682–691; Rose U.S. Pat No. 5,279,833; Brigham (1991) WO 91/06309; and Felgner et al. (1987) *Proc. Natl. Acad. Sci. USA* 84: 7413–7414).

It is recognized, however, that the kinesin motor modulators of this invention are relatively charged molecules. Both charge and molecule size tend to decrease cellular uptake and serum half-life. Consequently, in a preferred embodiment, it is desirable to package, complex, or otherwise combine the kinesin motor modulator with a delivery vehicle that preferably increases cellular uptake and/or serum half-life.

A wide variety of suitable vehicles are well known to those of skill. Thus, for example, the kinesin motor modulator can be complexed with, or encapsulated within, a charged lipid to form a net neutral composition. This will reduce clearance by the reticuloendothelial system and enhance cellular uptake.

In another embodiment, the kinesin motor modulators can be encapsulated within or complexed with microparticles which can be recognized and phagocytosed by a target cell thereby facilitating entry of the kinesin motor modulator into the cell. Other methods of facilitating entry include the use of fusion proteins, protein complexes, and masking charged sulfate groups with reversible chemical modification or counterions.

The size of particles and their mode of delivery determines their biological behavior. Strand et al. (1998) in *Microspheres-Biomedical Applications,* A. Rembaum, ed., pp 193–227, CRC Press have described the fate of particles to be dependent on their size. Particles in the size range of a few nanometers (nm) to 100 nm enter the lymphatic capillaries following interstitial injection, and phagocytosis may occur within the lymph nodes. After intravenous/intraarterial injection, particles less than about 2 microns will be rapidly cleared from the blood stream by the reticuloendothelial system (RES), also known as the mononuclear phagocyte system (MPS). Particles larger than about 7 microns will, after intravenous injection, be trapped in the lung capillaries. After intraarterial injection, particles are trapped in the first capillary bed reached. Inhaled particles are trapped by the alveolar macrophages. It will also be appreciated that microparticles, and other delivery vehicles can be targeted to specific cells and/or tissues (e.g., by conjugation with antibodies, or other cell or tissue specific ligands) or by the use of vehicles that have specific cell or tissue trophisms.

While the kinesin motor modulators of this invention are generally water soluble, some species are moderately insoluble. Those compounds that are water-insoluble or poorly water-are not well suited to conventional administration (e.g., by intravenous injection or oral administration). The parenteral administration of such pharmaceuticals can be achieved by emulsification of oil or lipid solubilized compound with an aqueous liquid (such as normal saline) in the presence of surfactants or emulsion stabilizers to produce stable microemulsions. These emulsions may be injected intravenously, provided the components of the emulsion are pharmacologically inert. For example, U.S. Pat. No. 4,073,943 describes the administration of water-insoluble pharmacologically active agents dissolved in oils and emulsified with water in the presence of surfactants such as egg phosphatides, pluronics (copolymers of polypropylene glycol and polyethylene glycol), polyglycerol oleate, etc. PCT International Publication No. WO85/00011 describes pharmaceutical microdroplets of an anaesthetic coated with a phospholipid, such as dimyristoyl phosphatidylcholine, having suitable dimensions for intradernal or intravenous injection.

Additionally, protein microspheres have been utilized as carriers of pharmacological or diagnostic agents. Microspheres of albumin have been prepared by either heat denaturation or chemical crosslinking. Heat denatured microspheres are produced from an emulsified mixture (e.g., albumin, the agent to be incorporated, and a suitable oil) at temperatures between 100° C. and 150° C. The microspheres are then washed with a suitable solvent and stored. Leucuta et al. (1988) *International Journal of Pharmaceutics* 41: 213–217, describe the method of preparation of heat denatured microspheres.

For certain of the therapeutic uses of the subject kinesin motor modulators, particularly cutaneous uses such as for the control of keratinocyte proliferation, direct (e.g., topical or injected) administration of the kinesin motor modulator will be appropriate. Accordingly, the subject kinesin motor modulator, alone or in combination with a delivery vehicle,, may be conveniently formulated for administration with a biologically acceptable medium, such as water, buffered saline, polyol (for example, glycerol, propylene glycol, liquid polyethylene glycol and the like) or suitable mixtures thereof. In preferred embodiments, the kinesin motor modulator is dispersed in lipid formulations, such as miscelles, which closely resemble the lipid composition of natural cell membranes to which the kinesin motor modulator is to be delivered.

As indicated above, the kinesin motor modulators are preferably combined with a pharmaceutically acceptable carrier for in vivo administration. Pharmaceutically acceptable carriers (excipients) can contain a physiologically acceptable compound that acts, for example, to solubilize the composition, and/or to stabilize the composition, and/or to increase or decrease the absorption of the agent. Physiologically acceptable compounds can include, for example, carbohydrates, such as glucose, sucrose, or dextrans, antioxidants, such as ascorbic acid or glutathione, chelating agents, low and/or high molecular weight proteins, compositions that reduce the clearance or hydrolysis of the kinesin motor modulator(s), or excipients or other stabilizers and/or buffers. Other physiologically acceptable compounds include wetting agents, emulsifying agents, dispersing agents or preservatives which are particularly useful for preventing the growth or action of microorganisms.

For those kinesin motor modulators that are lipid soluble the use of solubilizers and/or emulsifiers is often desired to produce aqueous kinesin motor modulator solutions or emulsions. Such solubilizers and emulsifiers are well known to those of skill in the art.

For example, lower alkyl alcohols having from 2 to 3 carbon atoms are useful as diluents or solvents for kinesin motor modulators in the preparation of stabilized kinesin motor modulator compositions of the invention. Particularly useful alcohols are selected from the group consisting of ethyl alcohol, n-propyl alcohol and mixtures thereof. These alcohols are useful generally in the proportions by weight of about 1 to about 25 percent, preferably about 3 to about 15 percent, more preferably about 4 to about 10 percent, and most preferably about 4 to about 6 percent by weight, all based upon the weight of the kinesin motor modulator. These alcohols are miscible in both water and many oils and can, therefore, be utilized as solvents for most of the forms of the fat-soluble kinesin motor modulators. These alcohols also serve to control the viscosity of the kinesin motor modulator composition and act as secondary emulsifiers. Additionally, the alcohols can act as freeze depressants maintaining the fluidity of the kinesin motor modulator composition at lower temperatures.

The emulsifier system optionally utilized in the kinesin motor modulator compositions of this invention can be selected from the various ionic or nonionic emulsifiers. The emulsifiers used must be acceptable as additives for oral administration and/or for intravenous administration and have no significant deleterious effect upon the kinesin motor modulator used therewith or upon the effectiveness of the lower alkyl alcohol utilized as a solvent or diluent.

The kinesin motor modulator based pharmacological compositions are preferably sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component. In, tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

It is recognized that the kinesin motor modulators, when administered orally, must be protected from digestion. This is typically accomplished either by complexing the kinesin motor modulator with a composition to render it resistant to acidic and enzymatic hydrolysis or by packaging the kinesin motor modulator in an appropriately resistant carrier such as a liposome. Means of protecting compounds from digestion are well known in the art (see, e.g., U.S. Pat. No. 5,391,377 describing lipid compositions for oral delivery of therapeutic agents)

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For example, parenteral injection liquid preparations can be formulated in solutions in aqueous polyethylene glycol solution.

Aqueous solutions suitable for oral use can be prepared by dissolving the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, and other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The concentration of kinesin motor modulators or other active ingredients in these formulations can vary widely, and will be selected primarily based on fluid volumes, viscosities, body weight and the like in accordance with the particular mode of administration selected and the patient's needs.

C) Dosages.

Where the kinesin motor modulator is used in a therapeutic context, (e.g., in the treatment of a condition characterized by cellular hyperproliferation), a therapeutically effective quantity of adocia-derived kinesin modulator is employed in treatment. A therapeutically effective quantity or dosage refers to a dosage adequate to ameliorate symptoms or signs of the disease or to provide effective prophylaxis without producing unacceptable toxicity to the patient. In general, an effective amount of the compound is that which provides either subjective relief of symptoms or an objectively identifiable improvement as noted by the clinician or other qualified observer.

The dosage of compounds used in accordance with this invention varies depending on the compound and the condition being treated. The age, weight, and clinical condition of the recipient patient; and the experience and judgment of the clinician, practitioner, or veterinarian administering the therapy are among the factors affecting the selected dosage. Other factors include the route of administration the patient, the patient's medical history, the severity of the disease process, and the potency of the particular compound.

Broadly, a dosing schedule is from about 2 mg to about 2000 mg two or three times a day. More typically, a dose is about 20mg to about 400 mg of compound given three times a day. A dosage range for topical treatment is about 0.1% to about 10% (weight/volume) in a physiologically acceptable eye drop applied one to five or even ten times a day.

It will be appreciated that such dosages are typically advisorial in nature and may be adjusted depending on the particular therapeutic context, patient tolerance, etc. Substantially higher dosages are possible by any selected route, for example, topical administration.

Typically, the dosage is administered at least once a day until a therapeutic or prophylactic result is achieved. Preferably, the dosage is administered twice a day, but more or less frequent dosing can be recommended by the clinician. Once a therapeutic result is achieved, the drug level can be modified for maintenance treatment. Under some conditions, the drug may be tapered or discontinued after the appearance of a therapeutic result. Occasionally, side effects warrant discontinuation of therapy.

V. Adocia-derived kinesin motor modulator kits.

In another embodiment, this invention provides kits for the practice of the methods of this invention. The kits preferably include one or more containers containing a adocia-derived kinesin motor modulator of this invention. The kit can optionally include a pharmaceutically acceptable excipient and/or a delivery vehicle (e.g., a liposome). The kinesin modulator may be provided suspended in the excipient and/or delivery vehicle or may be provided as a separate component which can be later combined with the excipient and/or delivery vehicle. The kit may optionally contain additional therapeutics to be co-administered with the kinesin motor modulator.

The kits may also optionally include appropriate systems (e.g. opaque containers) or stabilizers (e.g. antioxidants) to prevent degradation of the kinesin motor modulators by light or other adverse conditions.

The kits may optionally include instructional materials containing directions (i.e., protocols) providing for the use of a Adocia-derived kinesin motor modulator in the treatment of a disease in a mammal wherein the disease is characterized by cellular hyperproliferation. In particular the disease can include any one or more of the disorders described herein. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the present invention.

Example 1

Isolation of Adociasulfates.

The sponge Adocia (Haliclona) sp. (Collection # 95-100) was collected in Palau, Western Caroline Islands, and was quickly frozen. The frozen sponge (225 g) was diced and steeped in a mixture of dichloromethane (300 μL) and methanol (IL) for 24 h. The solids were removed by filtration and the solution was reduced in volume to 300 mL and extracted with dichloromethane (2×200 mL).

Figure 1B:
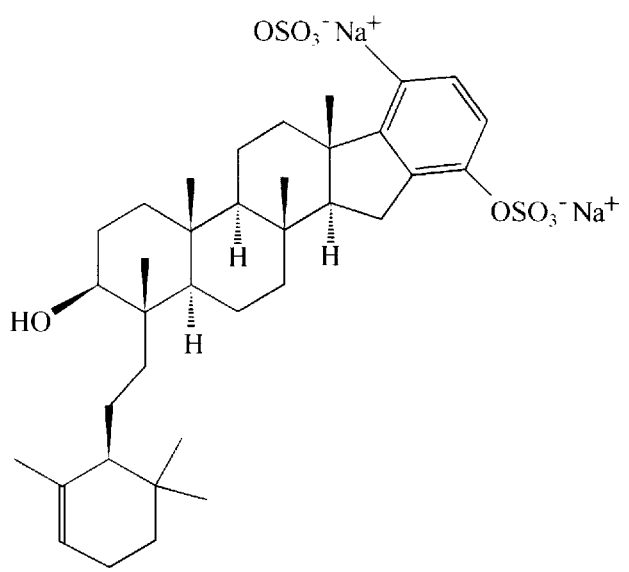
Figure 1C:
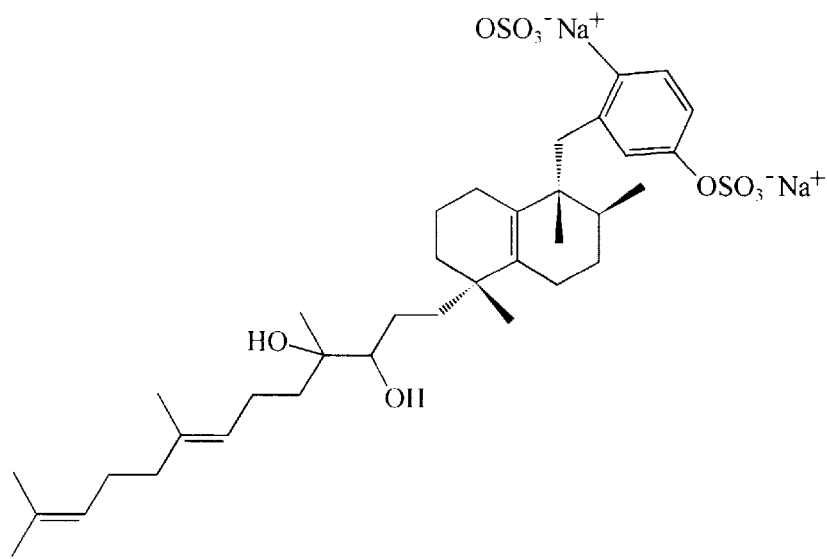
Figure 2:
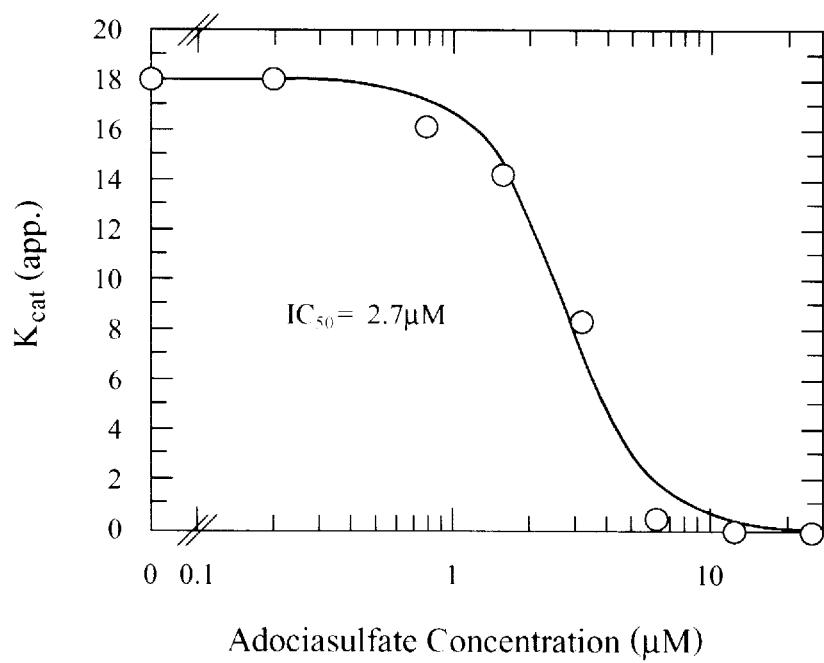
FIG. 2 shows adociasulfate-mediated inhibition of the microtubule stimulated ATPase of kinesin. The graph shows the dependence of the apparent $k_{cat}$ value of microtubule-stimulated kinesin ATPase in the presence of varying adociasulfate concentrations.

The aqueous phase was lyophilized to yield a pale yellow powder. The powder (1.0 g) was chromatographed twice on a reversed phase C18 Sep-Pak, using a gradient of 30% MeOH in $H_2O$ to 100% methanol (MeOH) as eluant, to obtain pure fractions containing adociasulfate-1 (FIG. 1a) and adociasulfate-2 (FIG. 1b) and a mixed fraction containing adociasulfates (FIGS. 1a, 1b, and 1c). The mixed fraction was separated by reversed phase HPLC using 1:1 MeOH-$H_2O$ as eluant. Pure fractions were combined to obtain adociasulfate-1 (13.5 mg), adociasulfate-2 (14.1 mg) and adociasulfate-3 (3.3 mg).

Example 2

Screening and Identification of Adocia-derived Kinesin Modulators.

Motility Assay.

TI-γ (a kinesin superfamily member from the fungus *Thermomyces lanuginosus*) was adsorbed to a glass coverslip and supplemented with a mixture of microtubules, 2 mM Mg-ATP, and sponge extracts in DMSO (5% final concentration). Motility was scored visually on a Zeiss Axioplan microscope sat up for DIC and fitted with an Argus 10 video processor (Hamanatsu).

Proteins.

All kinetic and binding measurements were performed on a bacterially expressed Drosophila kinesin heavy chain fragment containing amino acids 5–351 of the wild type protein and a hexahistidine tag at the C-terminus. Protein was purified from the soluble fraction of IPTG induced bacterial cells by a single round of affinity chromatography on Ni-NTA-agarose (Qiagen), concentrated by microfiltration, and frozen in small aliquots in liquid nitrogen.

Steady state kinetics.

Initial rate measurements were done at room temperature using a malachite green assay (Geladopoulos et al. (1991) *Anal. Biochem.*, 192: 112–116) modified to work in 96 well microtiter plates and scored on a plate reader at 650 nm. ATP concentration dependence and basal ATPase rate were determined by a coupled enzymatic assay with pyruvate kinase and lactate dehydrogenase monitoring changes in absorbance at 340 nm. Phosphate standards (650 μM–7μM) were included with each reading.

ATPase Assay (ADP release).

The percent of ADP released from the enzyme was determined by the methods of Hackney (see, e.g., Hackney (1994) *J. Biol. Chem.*, 2690: 16508–16511). Briefly, 80 μM kinesin was preincubated with $\alpha\text{-}^{32}PATP$ at room temperature for 15 min and than stored on ice. 1 μl aliquots of that mixture were diluted into 100 μl of "chase mix" containing 0.5 mg/ml pyruvate kinase, 2 mM phosphoenalpyruvate, and varying concentrations of adociasulfate. At different time points 5 μl aliquots of the chase mix were quenched in 100 μl 1 M HCV/1 mM ATP/1 mM ADP. The amount of ADP that became accessible to pyruvate kinase and was converted to ATP was determined by a thin layer chromatography on PEI-cellulose followed by phosphoimager quantitation.

In vivo Assays.

The effects of adociasulfate (FIG. 1a) injection in the early pre-cellular blastoderm embryo of *Drosophila melanogaster* were evaluated. Embryos were collected every 20 minutes, dechorionated, and prepared for injection (Santamaria (1986) paged 159–174 in *Drosophila, A Practical Approach*, D. B. Roberts, Eds., IRL Press, Oxford). The embryos were desiccated for 7 minutes and pressure injected with either the adociasulfate solution in injection buffer (5 mM KCI, 100 mM sodium phosphate pH 7.5), or with buffer alone as control The injected volume was less than 10% of the total embryonic volume. Sets of 20 embryos were injected in each batch and at least three such batches were injected for each different concentration of adociasulfate and control. The embryos were then allowed to develop for 20–30 minutes at room temperature inside a moist chamber and were subsequently fixed, devitelinized and immunostained for tubulin, and counter stained with 0.01 mg/ml DAPI (Ashburner, Drosophila, a Laboratory Manual, Cold Spring Harbor Laboratory Press, New York. (1989)).

Results.

Extracts from 268 marine sponges were initially tested for their ability to disrupt normal behavior of microtubules in a gliding motility assay. This screening method allowed immediate distinction between substances that affected microtubule movement and those that caused microtubule depolymerization or breakage. Active extracts from the initial screening were then tested for inhibition of the microtubule-stimulated kinesin ATPase.

The most promising candidates were extracts from the sponge Adocia sp. In the motility assay, these extracts disrupted microtubule attachment to the kinesin-coated surface, and totally abolished movement. The microtubule stimulated ATPase of kinesin was also completely inhibited.

Three active compounds in the extract were identified and isolated (see FIGS. 1a, 1b, and 1c). These specific compounds are referred to herein as adociasulfates while the generic compounds are referred to as Adocia compounds or Adocia kinesin modulators (e.g., inhibitors). The structure of the Adocia compounds or adociasulfates does not resemble that of nucleotide triphosphates. This indicates that the Adocia structures are different from known kinesin modulators. In addition, it is believed that the activity spectrum of the Adocia compounds is narrower than that of nucleotide triphosphates or analogues thereof.

To further investigate specificity, the adociasulfate of FIG. 1a was tested on a variety of ATPases using the ATPase activity assay described above. Of those tested, the only enzymes substantially inhibited by adociasulfate are members of kinesin superfamily (Table 2).

TABLE 2

| Concentrations of adociasulfate causing 50% inhibition of enzymatic activity. | |
|---|---|
| enzyme | C50 |
| rabbit kidney ATPase | >136 μM* |
| Apyrase | >136 μM* |

TABLE 2-continued

Concentrations of adociasulfate causing 50% inhibition of enzymatic activity.

| enzyme | C50 |
|---|---|
| Myosin II (EDTA)[A] | 75 μM |
| CENP-E | 10 μM[D] |
| K5-351[B] | 2 μM[E] |
| K411[C] | 2 μM[E] |
| TI-γ | 2 μM[E] |
| ncd | — |
| myosin | — |
| pyruvate kinase | — |

Figure 3:
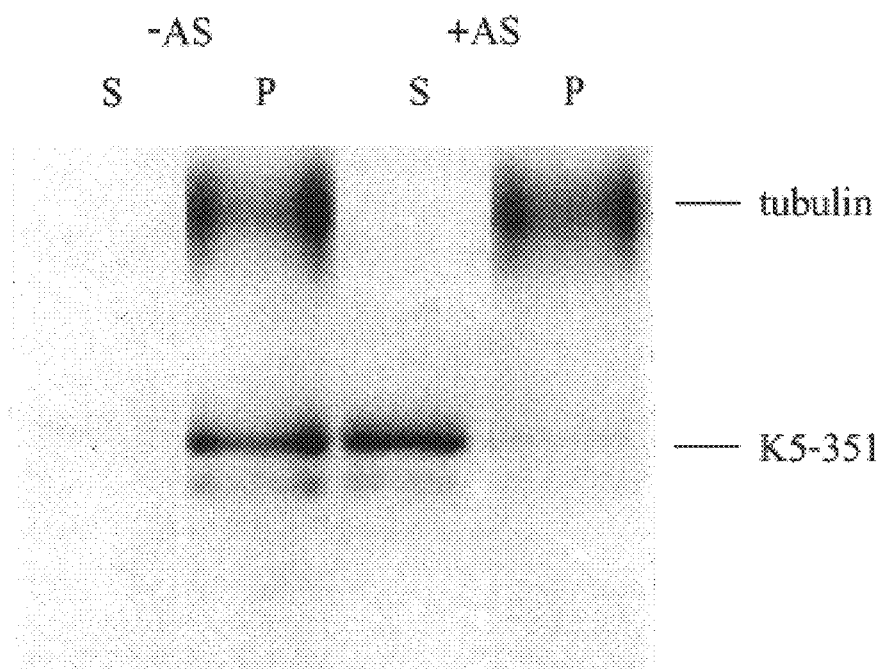
FIG. 3 shows that adociasulfate prevents binding of kinesin to microtubules. Monomeric kinesin protein K5-351 (3.5 $\mu$M), was preincubated with microtubules (3.6 $\mu$M), MgAMP-PNP (2 mM), with or without 35 $\mu$M adociasulfate (FIG. 1a). After 10 min the mixture was centrifuged at 80,000×g for 30 min, and supernatants (S) and pellets (P) were analyzed by SDS-PAGE.

*enzyme was not inhibited by 50% at the highest used inhibitor concentration of 136 μM.;
[A]EDTA activated ATPase;
[B]construct containing amino acids 5-351 of Drosophila kinesin;
[C]construct containing first 411 amino acids of Drosophila kinesin;
[D]at 6 μM tubulin;
[E]at 2 μM tubulin The behavior observed in the motility assay indicated that adociasulfates interfere with microtubule binding to the motor. This was tested by performing a kinesin-microtubule co-sedimentation assay in the presence of a nonhydrolysable ATP analog, AMP-PNP, with or without adociasulfate (FIG. 3). Addition of adociasulfate abolished binding of kinesin to microtubules under these conditions.

Figure 4A:
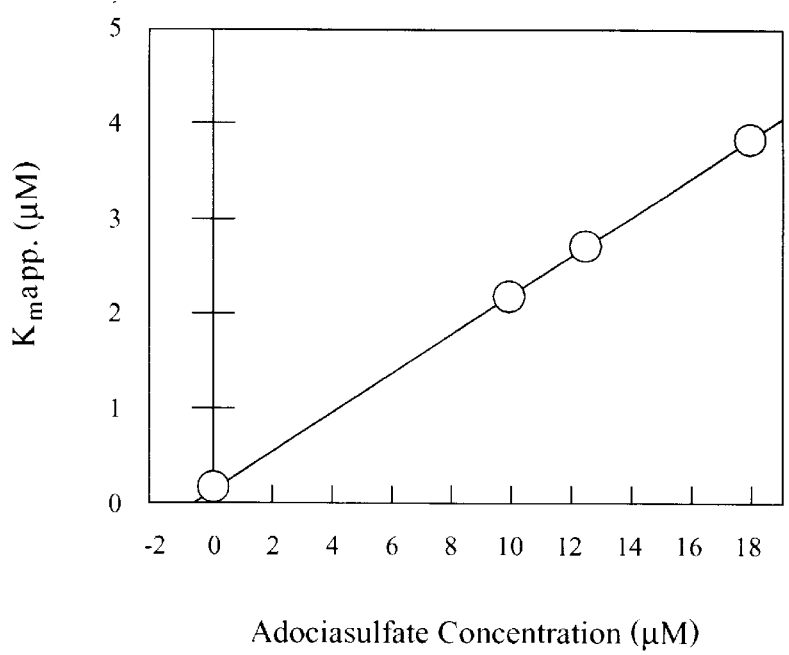
FIGS. 4a and 4b show that adociasulfate inhibition is competitive with microtubule, but not with ATP. ATP-concentration dependence was determined by a coupled enzymatic assay with pyruvate kinase and lactate dehydrogenase monitoring changes in absorbance at 340 nm (Huang et al. (1994) *J. Biol., Chem.,* 269: 16508–16511).

Consideration of the kinesin mechanochemical cycle suggests that the effect on microtubule binding could be induced either by looking the kinesin in a weakly-binding state resembling the kinesin-ADP intermediate by adociasulfate binding in the nucleotide pocket, or by direct interference with the microtubule-binding site. Steady state kinetic measurements demonstrated that the adociasulfate-induced inhibition is competitive with microtubules, and could be totally reversed by high microtubule concentrations (FIG. 4a).

Figure 4B:
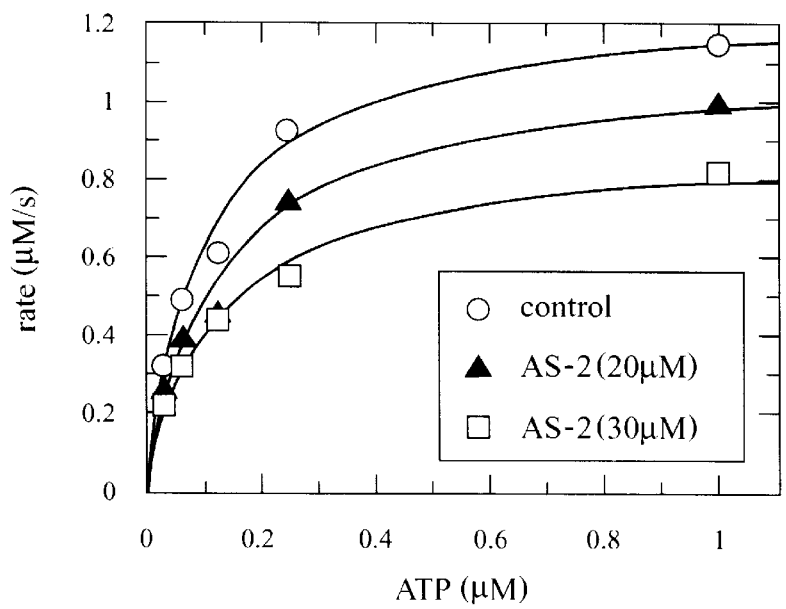

In contrast, varying the ATP concentration had no effect on the overall shape of the kinetic curves. $V_{max}$ was progressively lower at higher adociasulfate concentrations (FIG. 4b). An additional argument against adociasulfate binding at the nucleotide pocket comes from the lack of an inhibitory effect on the basal, non microtubule-stimulated rate of the kinesin ATPases. If adociasulfate interfered with nucleotide binding, or locked the enzyme in a particular nucleotide-bound state, ATP turnover in the absence of microtubule should be decreased. However, concentrations of up to 136 μM adociasulfate (the highest tested) did not inhibit the basal ATPase rate.

Figure 5A:
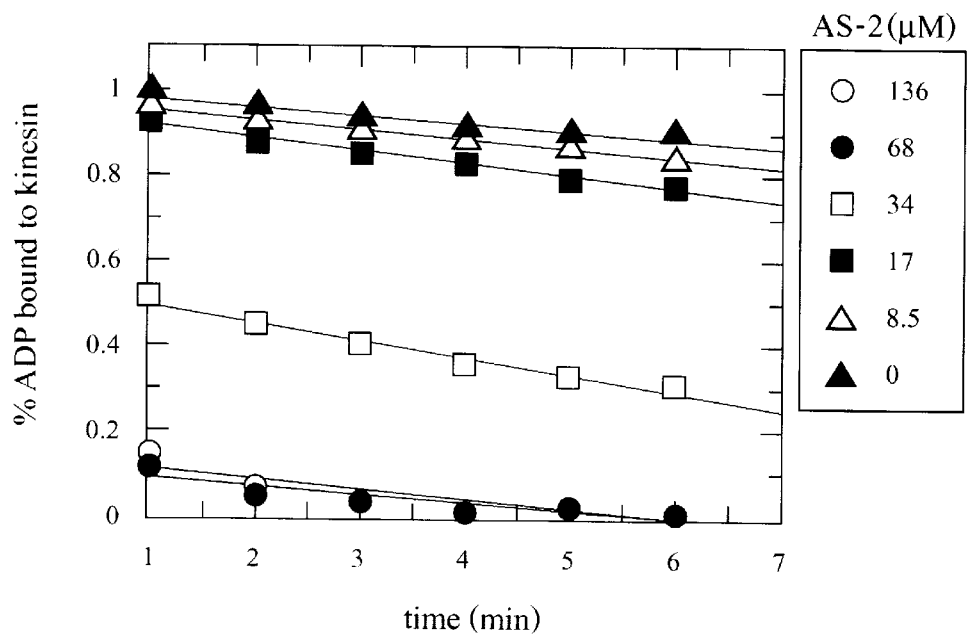
FIGS. 5a and 5b show that adociasulfates induce a burst of ADP release. To determine the percent of ADP released from kinesin (Hackney (1994) *J. Biol. Chem.,* 269: 16508–16511) 80 $\mu$M kinesin was preincubated with $\alpha$-$^{32}$p-ATP at room temperature for 15 minutes and then stored on ice. 1 $\mu$L aliquots of that mixture were diluted into 100 $\mu$L of "chase mix" containing 0.5 mg/ml pyruvate kinase, 2 mM phosphoenolpyruvate and varying concentrations of aldociasulfate (FIG. 1a). At different time points, 5 $\mu$L aliquots of the chase mix were quenched in 100 $\mu$L of 1 M HCl/1 mM ATP/1 mM ADP. The amount of ADP that became accessible to pyruvate kinase and was converted to ATP was determined by thin layer chromatography (TLC) on PEI-cellulose followed by phosphoimager (Molecular Dynamics) quantitation.
Figure 5B:
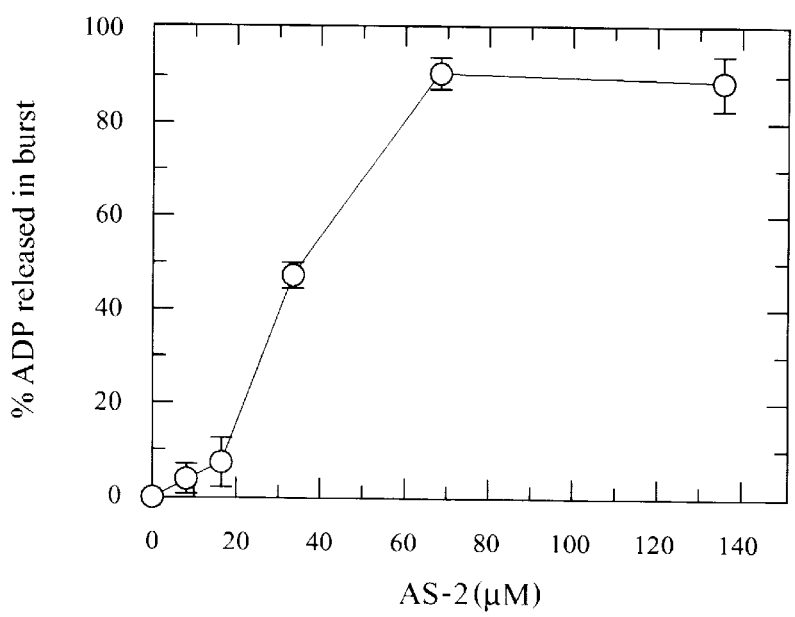

Microtubule binding to kinesin induced 1,000-fold stimulation of the basal TPase rate, owing primarily to accelerated ADP release. Is was tested whether adociasulfate binding to kinesin could mimic the effect of the microtubule by examining ADP release from kinesin in the presence of varying concentrations of adociasulfate. Indeed, bursts of ADP release were observed and their magnitude correlated positively with the concentration of adociasulfate (FIGS. 5a and 5b). The adociasulfate concentration at 50% of maximum burst is much higher than the $K_i$ determined in steady state microtubule competition assays. This discrepancy may reflect different affinities for adociasulfate in different nucleotide states of kinesin. Steady state kinetic measurements of $K_i$ reflect the affinity of the most tightly bound state of the entire cycle, which includes several kinesin-nucleotide intermediates (K-ATP, K-ADP-Pi, K-ADP etc.).

In contrast, the ADP release experiment with adociasulfate involved only one state, K-ADP. It is intriguing that this state also has the lowest affinity for the microtubule. It was initially surprising that adociasulfate did not stimulate the kinesin basal ATPase even though it induced ADP release. However, during steady state kinetic measurements, each single headed kinesin molecule must undergo several cycles of attachment-detachment to microtubule subunits. In contrast, AS presumably remains bound through multiple enzymatic turnovers. The physiological equivalent of such a state would be a kinesin molecule permanently attached to a single tubulin dimer, a state for which no kinetic data exist. However, if the adociasulfate binding to kinesin resembles microtubule binding, the initial association event should result in a burst of ADP release as observed.

Example 3

In vivo effects of adociasulfates.

The in vivo effects of adociasulfate were also investigated. Preliminary experiments demonstrated that AS had no effect on HeLa cells proliferation. However, because it is a fairly large molecule (MW 738) with two charged sulfate moieties, adociasulfate may have problems crossing the cell membrane. This difficulty can be alleviated by direct injection of adociasulfate into a cell.

Drosophila embryos, a well characterized and sturdy system, were thus used for direct injection studies. In Drosophila embryos the first 13 rounds of cell division take place in a syncitium during the first two hours after fertilization. The first seven of these divisions are synchronized and occur at the center of the egg yolk. During the remaining divisions, most nucleic move to the surface of the egg and continue to divide for the next three times in partially open cell buds (see, Campos-Ortega et al. (1985) *The embryonic development of Drosophila melanogaster,* Springer Verlag). Thus, any drug injected in to the Drosophila will have access to a large number of mitotic nuclei at the surface of the egg during the last three divisions.

Three different concentrations of adociasulfate were injected (1 mM, 0.1 mM, and 0.05 mM) in combination with 1 mg/ml tetramethylrhodamine (TMR)-tubulin. Injection of up to 0.1 mM adociasulfate arrested all nuclear divisions immediately at the point of injection. Injection of 0.05 mM adociasulfate caused less severe phenotypes that allowed observation of more distinct abnormalities. Spindles and microtubule asters without chromosomes were found at the site of injection. Mats of unattached microtubules and chromosomes apparently detached from the spindle were also observed. These effects could be accounted for by loss of function of various members of the kinesin superfamily.

These results demonstrate that adociasulfate specifically modulats kinesin activity by interfering with microtubule binding. This mechanism is unlike that of any know kinesin (or other motor) inhibitor. Without being bound to a theory it is believed that adociasulfate modulats binding by emulating tubulin binding to a portion of the microtubule binding site of kinesin. In addition, adociasulfate is a potent toxin, which, when delivered intracellularly, may ablate several, if not all, aspects of kinesin-superfamily mediated transport.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference.

What is claimed is:

1. A method of identifying a compound that specifically modulates a kinesin motor at a microtubule binding site, said method comprising the steps of:
   (i) assaying for competitive inhibition of said motor by said compound at a kinesin ATPase site;
   (ii) assaying for competitive inhibition of said motor by said compound at a microtubule binding site;
   (iii) identifying a small compound as a kinesin modulator specific to a microtubule binding site when said small compound is a competitive modulator at said microtubule binding site, but not at said ATPase site.

2. The method of claim 1, wherein said assaying comprises detecting ATPase activity of said kinesin motor.

3. The method of claim 1, wherein compound is a polypeptide.

4. The method of claim 1, wherein compound is a nucleic acid.

5. The method of claim 1, wherein compound is an antibody.

6. The method of claim 1, wherein compound is a small organic molecule.

7. The method of claim 1, wherein compound is an inorganic molecule.

8. A method of modulating kinesin motor activity, said method comprising contacting said kinesin motor with a small organic molecule that competitively inhibits said kinesin motor at a microtubule binding site.

9. A method of identifying an agent that modulates the kinesin inhibitory activity of an Adocia kinesin inhibitor, said method comprising:
   (i) contacting a microtubule, a kinesin motor, and an Adocia kinesin inhibitor with a candidate agent; and
   (ii) detecting a change in the kinesin inhibitory activity of the Adocia kinesin inhibitor resulting from said contacting, wherein a change indicates the identification of an agent that modulates the kinesin inhibitory activity of the Adocia kinesin inhibitor.

10. A method of identifying an agent that interferes with the binding of an Adocia kinesin inhibitor with a kinesin, said method comprising:
    (i) contacting a kinesin and an Adocia kinesin inhibitor with a candidate agent; and
    (ii) detecting a decrease in the binding of the Adocia kinesin inhibitor with the kinesin resulting from said contacting, wherein a decrease indicates the identification of an agent that interferes with the binding of the Adocia kinesin inhibitor and the kinesin.

11. A complex comprising an Adocia kinesin inhibitor and a kinesin.

12. A method of modulating cellular growth in an organism, said method comprising administering to said organism a composition comprising a pharmaceutically acceptable carrier the compound of claim 1 in a quantity sufficient to alter said cellular growth in an organism.

13. The method of claim 12, wherein said organism is an animal.

14. The method of claim 12, wherein said organism is an plant.

15. A method of claim 8 wherein the competitive inhibition of the microtubule binding site involves contacting the kinesin motor with an Adocia kinesin modulator.

16. A method of claim 8 wherein the small organic molecule is a part of a combinatorial library when contacted with the kinesin motor.

17. A method of claim 8 wherein the small organic molecule has a terpene substituent.

* * * * *

UNITED STATES PATENT AND TRADEMARK OFFICE
CERTIFICATE OF CORRECTION

PATENT NO. : 6,207,403 B1
DATED : March 27, 2001
INVENTOR(S) : Goldstein et al.

It is certified that error appears in the above-identified patent and that said Letters Patent is hereby corrected as shown below:

Title page,
Item [56], References Cited, OTHER PUBLICATIONS, please delete "2070" and insert -- 207 --; please delete "197" and insert -- 1197 --; and please delete "19991" and insert -- 1991 --.
Item [57], ABSTRACT,
Line 2, please italicize "*Adocia sp.*";
Line 5, please italicize "*in vitro*"; and
Lines 5-6, please italicize "*in vivo.*"

Column 1,
Line 26, please delete "metabolic often" and insert -- metabolic compounds often --.
Line 34, please delete "nuclibranches" and insert -- nudibranches --.
Lines 56-64, please delete "Nat, Prod. Rep" and insert -- Nat. Prod. Rep --.

Column 3,
Line 15, please delete "on" and insert -- one --.

Column 5,
Line 7, please delete "he" and insert -- the --.
Line 10, please delete "assays" and insert -- Assays --.
Line 52, please delete "n" and insert -- an --.
Line 56, please delete "ro" and insert -- or --.

Column 7,
Lines 3-4, please delete "memingioma, ... sarcomass" and insert -- meningioma, ... sarcomas --.
Line 8, please delete "Frontotemporal Dementias" and insert -- Fronto and Temporal Dementias --.
Line 12, please delete "sell" and insert -- well --.
Line 19, please delete "increaing" and insert -- increasing --.
Line 40, please delete "microtubule" and insert -- microtubules --.

Column 8,
Line 58, please delete "pato" and insert -- potato --.
Line 67, please delete "exipient" and insert -- excipient --.

UNITED STATES PATENT AND TRADEMARK OFFICE
CERTIFICATE OF CORRECTION

PATENT NO. : 6,207,403 B1
DATED : March 27, 2001
INVENTOR(S) : Goldstein et al.

It is certified that error appears in the above-identified patent and that said Letters Patent is hereby corrected as shown below:

Column 9,
Line 26, please delete "miro" and insert -- micro --.

Column 11,
Line 15, please delete "the" and insert -- The --.

Column 14,
Lines 57-58, please delete "VI, , more" and insert -- VI, more --.

Column 17,
Lines 21-22, please delete "modulat kinesin" and insert -- modulate kinesin --.
Line 23, please delete "activity a microtubule" and insert -- activity of a microtubule --.
Line 44, please delete "e.g..," and insert -- e.g., --.
Line 64, please delete "example" and insert -- Example --.

Column 18,
Lines 62-64, please delete "adocia-derived … assays," and insert --
*Adocia*-derived … assays, --.

Column 20,
Line 19, please delete "acid addition salt" and insert -- acid salt --.
Line 62, please delete "Press have" and insert -- Press, have --.
Line 67, please delete "intraarterial" and insert -- intra-arterial --.

Column 21,
Line 5, please delete "intraarterial" and insert -- intra-arterial --.
Line 16, please delete "water-are" and insert -- water-soluble are --.
Lines 33-34, please delete "intradernal" and insert -- intradermal --.
Line 41, please delete "100° C. and" and insert -- 100° C and --.

Column 24,
Line 15, please delete "about 20mg to" and insert -- about 20 mg to --.

Column 28,
Line 28, please delete "syncitium" and insert -- syncytium --.
Line 31, please delete "nucleic" and insert -- nuclei --.
Lines 51 and 54, please delete "modulats" and insert -- modulates --.
Line 52, please delete "know kinesin" and insert -- known kinesin --.

UNITED STATES PATENT AND TRADEMARK OFFICE
CERTIFICATE OF CORRECTION

PATENT NO. : 6,207,403 B1
DATED : March 27, 2001
INVENTOR(S) : Goldstein et al.

It is certified that error appears in the above-identified patent and that said Letters Patent is hereby corrected as shown below:

Column 30,
Beginning at line 17, replace claim 12 with the following claim:
-- 12. A method of modulating cellular growth in an organism, said method comprising administering to said organism a composition comprising a pharmaceutically adaptable carrier and the compound having a formula:

[Formula]

wherein $R^1$ and $R^2$ are either independent monovalent moieties independently selected from the group of H, hemiterpenes, terpene monomers and terpene oligomers such that at least one of $R^1$ and $R^2$ is not H,
    or $R^1$ and $R^2$ are combined for form a single divalent terpene moiety selected from the group consisting of hemiterpenes, terpene monomers and terpene oligomers;
    $X^1$ and $X^2$ are the same or different and are anionic derivatives of an organic group, an inorganic, group or a group which is a combination of organic and inorganic groups;
    $Y^{+n}$ is an organic or inorganic cation;
    m is either 1 or 2; and
    n is either 1 or 2;
in a quantity sufficient to alter said cellular growth in an organism. --
Please insert the following chemical structure in place of "[Formula]" in claim 12 on sheet 1.

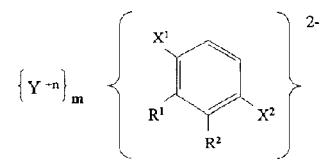

Signed and Sealed this

Sixth Day of July, 2004

JON W. DUDAS
*Acting Director of the United States Patent and Trademark Office*